(12) United States Patent
Griffin

(10) Patent No.: US 9,488,782 B2
(45) Date of Patent: Nov. 8, 2016

(54) REDIRECTING ELECTROMAGNETIC RADIATION

(71) Applicant: InnovaQuartz LLC, Pheonix, AZ (US)

(72) Inventor: Stephen E. Griffin, Peoria, AZ (US)

( * ) Notice: Subject to any disclaimer, the term of this patent is extended or adjusted under 35 U.S.C. 154(b) by 0 days.

(21) Appl. No.: 14/937,427

(22) Filed: Nov. 10, 2015

(65) Prior Publication Data

US 2016/0178844 A1 Jun. 23, 2016

Related U.S. Application Data

(63) Continuation-in-part of application No. 14/578,739, filed on Dec. 22, 2014, now Pat. No. 9,323,005.

(51) Int. Cl.
| | |
|---|---|
| *G02B 6/32* | (2006.01) |
| *G02B 6/26* | (2006.01) |
| *A61B 18/24* | (2006.01) |
| *C03B 37/012* | (2006.01) |
| *A61B 18/22* | (2006.01) |
| *A61B 17/00* | (2006.01) |
| *A61B 18/00* | (2006.01) |

(52) U.S. Cl.
CPC .............. *G02B 6/262* (2013.01); *A61B 18/24* (2013.01); *C03B 37/01211* (2013.01); *G02B 6/32* (2013.01); *A61B 18/22* (2013.01); *A61B 2017/00061* (2013.01); *A61B 2018/00386* (2013.01); *A61B 2018/00404* (2013.01); *A61B 2018/00511* (2013.01); *A61B 2018/00547* (2013.01); *A61B 2018/00577* (2013.01); *A61B 2018/00589* (2013.01); *A61B 2018/00625* (2013.01); *A61B 2018/00785* (2013.01); *A61B 2018/00982* (2013.01); *A61B 2018/2211* (2013.01); *A61B 2018/2244* (2013.01); *A61B 2018/2266* (2013.01); *A61B 2018/2272* (2013.01); *A61B 2018/2277* (2013.01)

(58) Field of Classification Search
CPC ......... G02B 6/32; G02B 6/262; A61B 18/22
USPC .......................................................... 385/33
See application file for complete search history.

(56) References Cited

U.S. PATENT DOCUMENTS

| | | | |
|---|---|---|---|
| 4,669,467 A | 6/1987 | Willett et al. | |
| 4,672,961 A | 6/1987 | Davies | |
| 4,732,448 A | 3/1988 | Goldenberg | |
| 4,740,047 A | 4/1988 | Abe et al. | |
| 5,061,265 A | 10/1991 | Abela et al. | |
| 5,074,632 A | 12/1991 | Potter | |
| 5,269,777 A | 12/1993 | Doiron et al. | |
| 5,292,320 A | 3/1994 | Brown et al. | |
| 5,343,543 A | 8/1994 | Novak et al. | |
| 5,354,294 A | 10/1994 | Chou | |
| 5,428,699 A | 6/1995 | Pon | |
| 5,449,357 A * | 9/1995 | Zinnanti ............ | A61M 1/0062 604/21 |
| 5,486,171 A | 1/1996 | Chou | |

(Continued)

*Primary Examiner* — Jerry Blevins
(74) *Attorney, Agent, or Firm* — Synthesis Intellectual Property LLC

(57) ABSTRACT

Herein is described a side firing optical device for minimal output reflections (scatter) in a one-piece lateral output assembly within which a transmitting optical fiber conduit is disposed providing redirected electromagnetic radiation with operator control of the output beam characteristics. The herein disclosed lateral redirecting device permits ergonomic free rotation of the lateral output beam with positive orientation, provides focus-control of the output beam spot size and/or focus, and provides resposable components, both intraoperatively and interoperatively.

19 Claims, 16 Drawing Sheets

(56) References Cited

U.S. PATENT DOCUMENTS

| | | |
|---|---|---|
| 5,495,541 A | 2/1996 | Murray et al. |
| 5,496,307 A | 3/1996 | Daikuzono |
| 5,496,308 A | 3/1996 | Brown et al. |
| 5,498,260 A | 3/1996 | Rink et al. |
| 5,509,917 A | 4/1996 | Cecchetti et al. |
| 5,512,078 A | 4/1996 | Griffin |
| 5,530,780 A | 6/1996 | Ohsawa |
| 5,537,499 A | 7/1996 | Brekke |
| 5,562,657 A | 10/1996 | Griffin |
| 5,571,099 A | 11/1996 | Purcell et al. |
| 5,695,583 A | 12/1997 | Bergh et al. |
| 5,807,390 A | 9/1998 | Fuller et al. |
| 5,824,005 A | 10/1998 | Motamedi et al. |
| 6,246,817 B1 | 6/2001 | Griffin |
| 6,270,492 B1 | 8/2001 | Sinofsky |
| 6,284,085 B1 | 9/2001 | Gwo |
| 6,398,778 B1 | 6/2002 | Gu et al. |
| 6,522,806 B1 | 2/2003 | James et al. |
| 6,687,436 B2 | 2/2004 | Griffin |
| 6,712,526 B1 | 3/2004 | Fleenor |
| 6,829,411 B2 | 12/2004 | Easley |
| 6,986,764 B2 | 1/2006 | Davenport et al. |
| 7,463,801 B2 | 12/2008 | Brekke et al. |
| 7,909,817 B2 | 3/2011 | Griffin et al. |
| 8,073,297 B2 | 12/2011 | Griffin |
| 2005/0165279 A1 | 7/2005 | Adler et al. |
| 2006/0282068 A1* | 12/2006 | Griffin .................. A61B 18/22 606/13 |
| 2006/0291061 A1 | 12/2006 | Iyama et al. |
| 2007/0106286 A1 | 5/2007 | Harschack et al. |
| 2008/0287936 A1 | 11/2008 | Stinson et al. |
| 2010/0135617 A1 | 6/2010 | Novak et al. |
| 2011/0038580 A1 | 2/2011 | Griffin |
| 2012/0130275 A1* | 5/2012 | Chudzik ............ A61B 10/0275 600/567 |

* cited by examiner

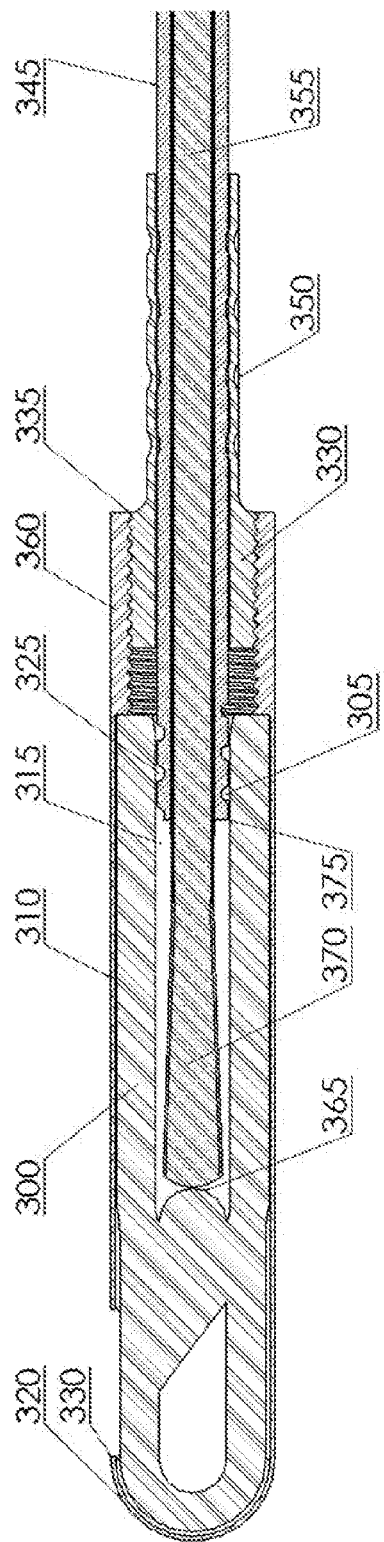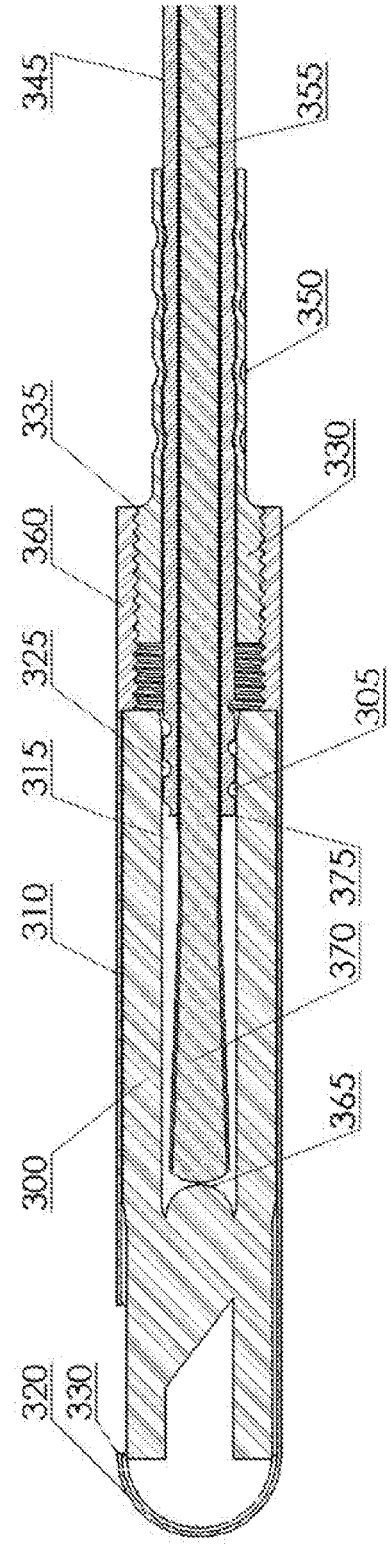
FIG. 10A
FIG. 10B
FIG. 10

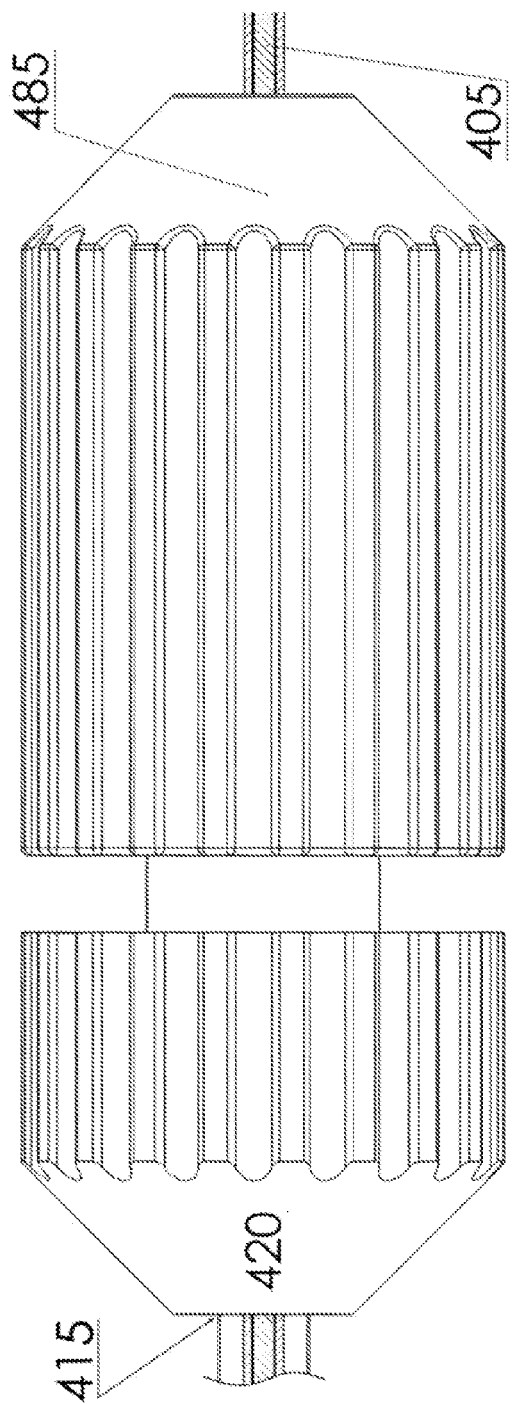
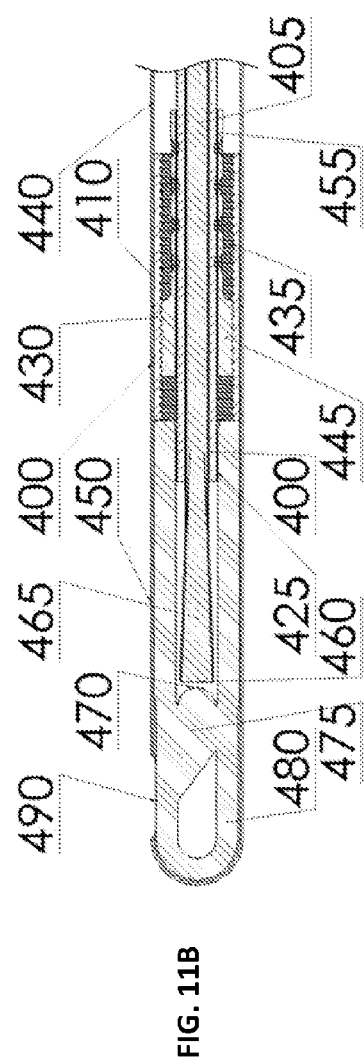

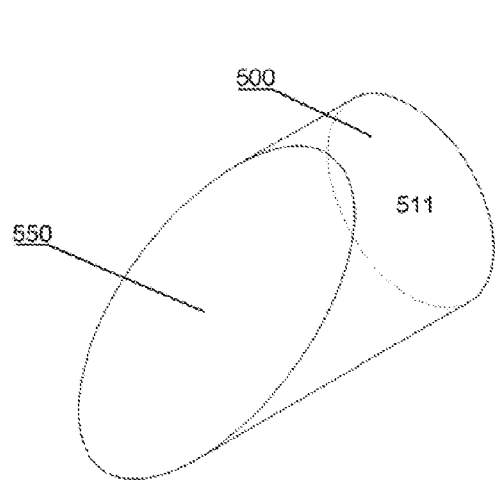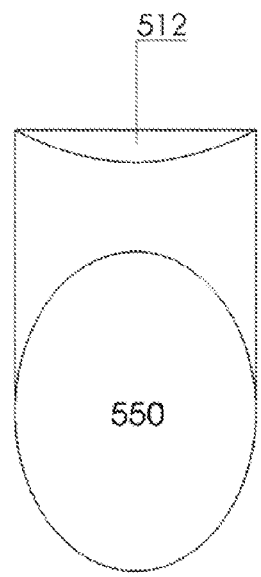
FIG. 14A　　　　　　　　　FIG. 14B
FIG. 14
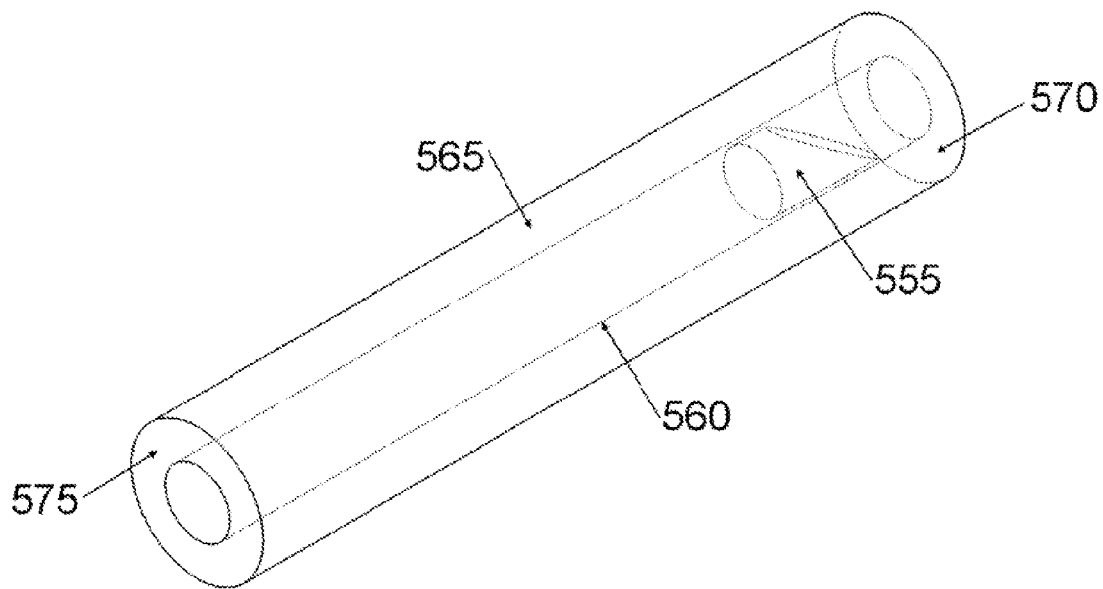
FIG. 15

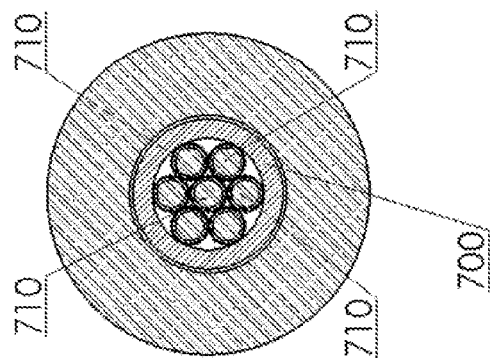
FIG. 17A
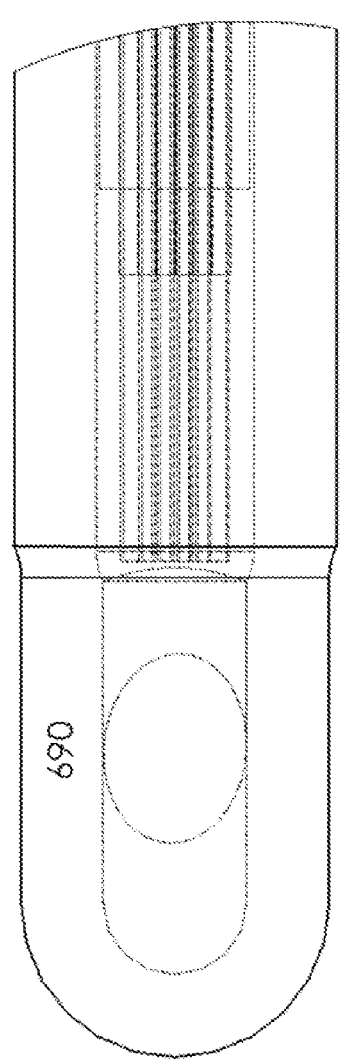
FIG. 17B
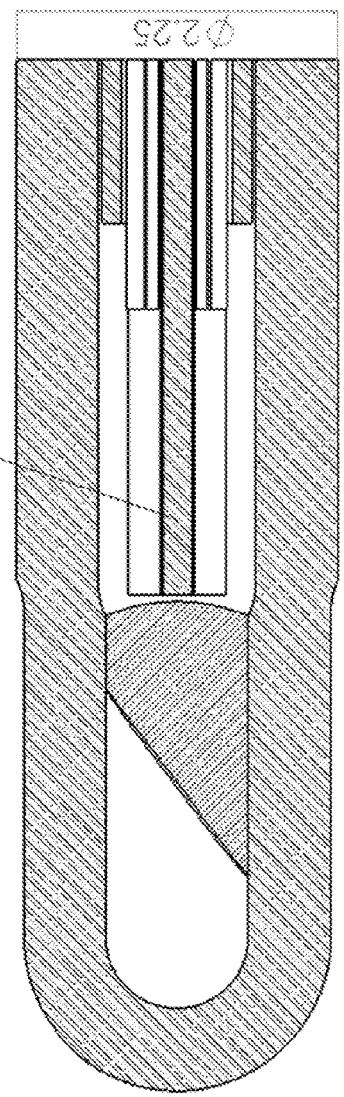
FIG. 17C
FIG. 17

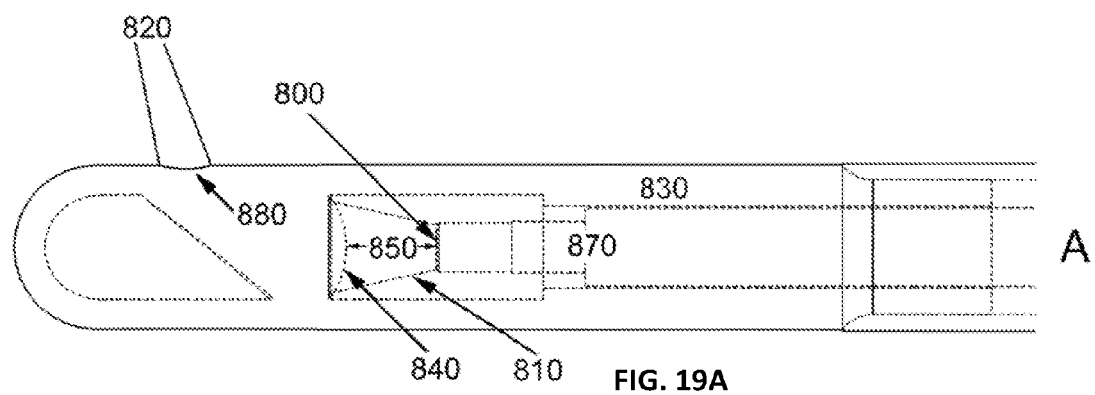
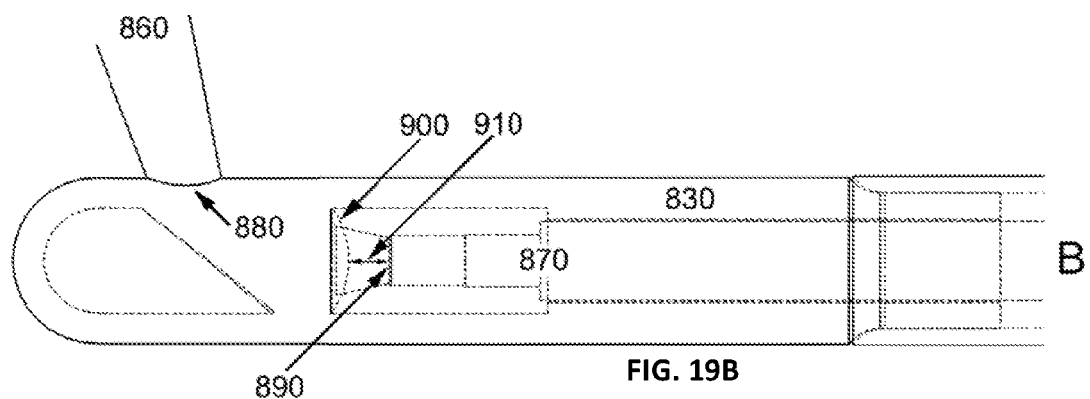
FIG. 19

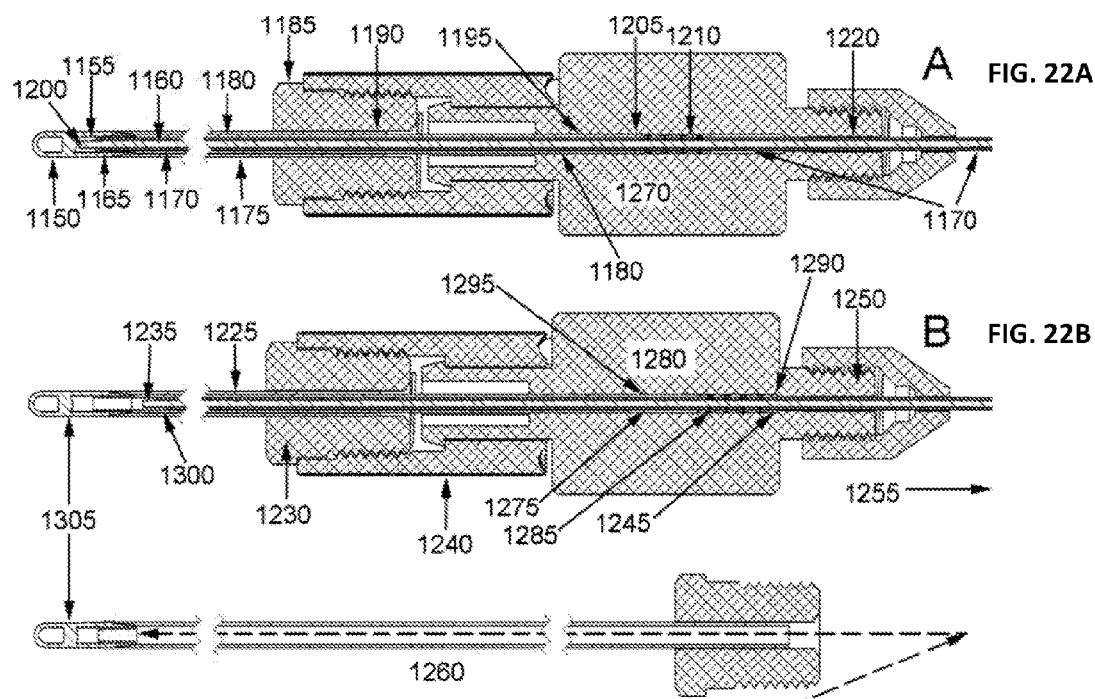
FIG. 22
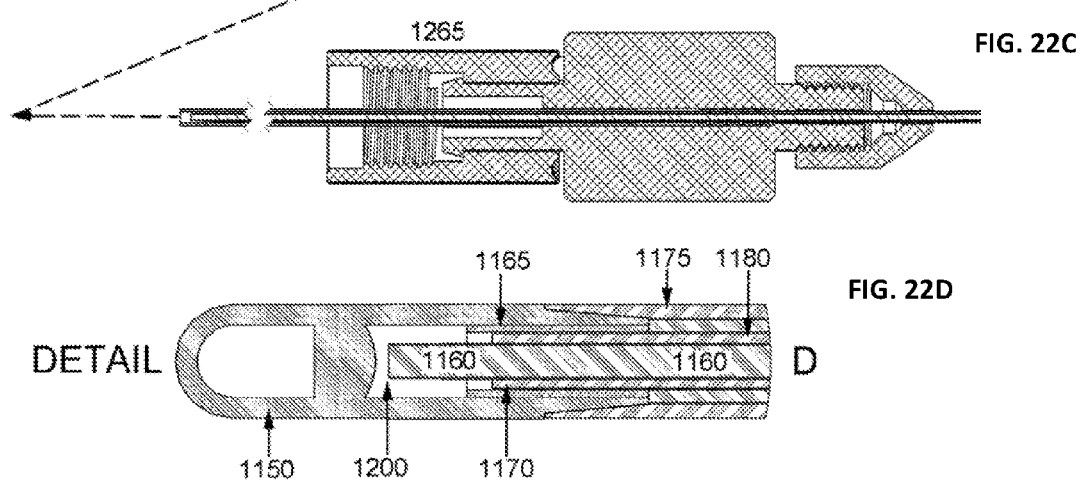

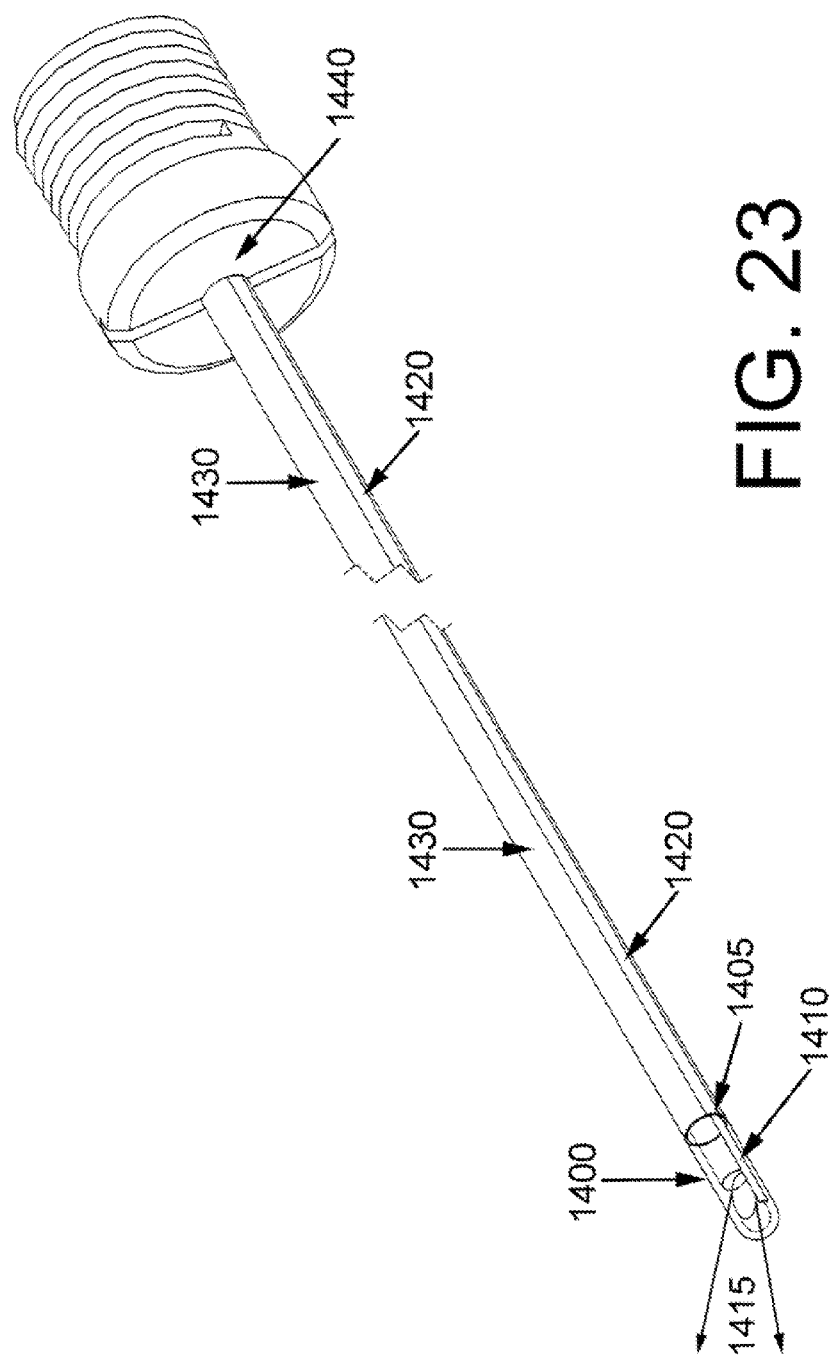

REDIRECTING ELECTROMAGNETIC RADIATION

CROSS-REFERENCE TO RELATED APPLICATIONS

This disclosure claims the benefit of priority to U.S. patent application Ser. No. 14/578,739, filed 22 Dec. 2014, the disclosure of which is incorporated herein in its entirety.

FIELD OF THE INVENTION

This invention is directed to fiber optic devices, and their manufacture, for the lateral radiation of electromagnetic radiation (e.g., lasers).

BACKGROUND

Electromagnetic energy, such as laser light, is used to perform various medical procedures including, for example, the vaporization of hyperplastic prostate tissues. One optical device that is used in surgical tools that perform such medical procedures is a side fire optical fiber device, also known as a lateral delivery device.

Lateral delivery optical fiber devices are typically used to redirect delivered electromagnetic radiation in an off-axis direction from the longitudinal axis of the delivery fiber, typically at an angle of 70-90 degrees off axis. Conventional side fire optical devices operate by reflecting the electromagnetic radiation off of a beveled optical surface that is machined and polished directly upon the transmitting optical fiber conduit, exploiting total reflection at or below the critical angle as described by Snell's Law. The conditions for total reflection are typically maintained by protecting the output bevel with a circumferential protective cap typically made of fused quartz or fused silica. The redirected output laser light is transmitted through a transmitting surface on the protective cap to the surgical site.

During surgery, the surface of the cap is subjected to cycles of rapid heating and cooling as well as sustained heating. Thermal cycling can induce stresses in the cap that are large enough to induce fracturing, particularly where the cap harbors residual stress from manufacturing, i.e. the external cap has not been annealed following melt processing as is the case in U.S. Pat. No. 5,537,499 (Brekke), U.S. Pat. No. 5,562,657 (Griffin), U.S. Pat. No. 7,463,801 (Brekke and Brucker), and U.S. Pat. No. 8,073,297 (Griffin). Both transient and sustained high temperatures at the transmitting surface of the cap accelerate the endothermic absorption of alkali metal ions within the quartz that form the cap, lowering viscosity sufficiently to permit rearrangement of the amorphous glass into high crystobalite; the cap undergoes devitrification.

These thermally mediated failure modes are more problematic when newer surgical lasers that produce significantly higher average powers are utilized, e.g. 120 W holmium laser energy (2140 nm), 180 W "Greenlight" laser energy (523 nm), 250 W diode laser energy (980 nm), 200 W thulium fiber laser energy (2000 nm) and further magnified when the device is involved in tissue contact surgery. The stresses in the side fire optical devices often result in the cap cracking, shattering or perforation by sloughing off of highly localized and intense devitrification.

Lateral delivery optical fibers for surgery have been described and produced for decades. Early lateral delivery fibers were simple in construction FIG. 1: an optical fiber 30 polished at an off-axis angle 15 of between 35 and 40 degrees about which a closed end 5 transparent tube 10, akin to a tiny test tube, is affixed (the tube is often called a "protective cap", the surface through which the light exits being referred to the "transmissive surface"). Deficiencies with this simple design were quickly recognized and strategies designed to mitigate these deficiencies were implemented with varying degrees of success. The example in FIG. 1 illustrates an embodiment of an invention first described in Japanese Pat. No. 61-64242 and later in U.S. Pat. No. 4,740,047 (Abe, et al.) where the original cylindrical transmissive surface of the cap, and the cap surface 180 degrees opposing the transmissive surface 20, are modified to planar surfaces.

As illustrated in FIG. 2, some rays of light imparting the curved side of an optical fiber after reflecting from the bevel surface within the simplest lateral delivery fibers encounter angles at or near the critical angle for total reflection (rays C and D in FIG. 3A) as defined by Snell's Law such that a significant portion of the energy that encounters the reflective bevel tip does not exit the fiber in the desired direction, but undergoes complex reflections within the tip instead, eventually exiting in a variety of directions other than the desired direction, with roughly 20% of the errant energy leaking in roughly the opposite direction from the desired output. Referring to FIG. 3A and FIG. 4, reflected rays imparting the cylindrical cladding 70 to air interface near the outer edge of the fiber core 60, as represented by rays C and D, are completely reflected and encounter the cylindrical wall again at low angles, only to be reflected again until, at points 80 and 90, where the rays encounter the bevel face once more, they are refracted and transmitted Ct and Dt out of the fiber tip in the wrong direction. More central rays as represented by A and B, are refracted by the cylindrical fiber's glass to air interface and transmitted At and Bt in the desired direction. All rays also undergo Fresnel reflections Af, Bf, Cf and Of upon ultimately exiting the fiber tip.

These complex reflections are repeated where the diameter of the fiber (glass diameter, usually the cladding) closely matches the diameter of the protective cap bore (which is not the case in Abe FIG. 1, due to the use of a relatively thick buffer coating of silicone 35 in optical fiber of the era), at the air to cap glass interface. Additional contributions to scattering in directions other than the intended output results from Fresnel reflection at the fiber core to cladding interface 65 (typically minor due to closely matched refractive indices), the cladding to air interface, the air to protective cap interface and the cap to working environment interface (again, minor due to the much closer match of the refractive indices of glass and saline irrigation fluid versus those for glass and air).

Additional distortion of the output results from the non-orthogonal off axis angle of emission and the cylindrical lens effects of the curved surfaces in the output pathway. In total, roughly 28% FIG. 2 of the energy imparting the fiber bevel exits at angles that are surgically useless, and potentially harmful, while the energy that is emitted in the desired direction is highly distorted. Rather than a round spot that diverges symmetrically, the spot is typically reminiscent of a crab with a roughly oval center (body) with radiating streaks (legs) and divergence is highly asymmetric.

Abe, et al. describe a strategy to mitigate the problem of unwanted reflections within the lateral fiber structure by eliminating the curvature of the cap outer diameter and equipping the transmissive surface with an antireflective coating and the surface 180 degrees opposing the transmissive surface with reflective coatings. This strategy does considerably reduce the output that is 180 degrees opposite of the desired direction but does not correct the distortion and fragmentation of the output in the desired direction. The expensive optical coatings are also short lived, being easily damaged in the surgical environment.

U.S. Pat. No. 5,428,699 (Pon) describes a more elegant, yet partial solution to the problem of unwanted reflections within the side fire fiber output FIG. 3B. Recognizing that the closely matching curvature of the fiber core and fiber cladding was the source of most of the exit angles at or near the critical angle, Pon pointed out that equipping the fiber with a thicker cladding 71 would greatly reduce these unwanted, complex reflections by displacing the glass to air interface away from the core 61. An embodiment of the invention described in Pon (Laserscope's LDD-Stat and other branding) was highly successful in the marketplace over the bulk of the '699 patent lifetime, in spite of the high cost resulting from using very expensive 1.4 CCDR (Cladding to Core Diameter Ratio) fiber, because the invention reduced the unwanted scatter output and distortions of the output spot by almost 75%.

Roughly contemporaneous with Pon, two patents, Brekke '499 FIG. 5 and Griffin '657 FIG. 6, taught another strategy for reducing unwanted reflections in side firing fibers: fusion of the fiber's outer glass diameter to the protective cap's inner diameter. Eliminating the large differences in refractive indices in the output path essentially eliminated the unwanted critical angle reflections (referred to as "Snell reflections" hereafter), Fresnel reflections and cylindrical distortions of the output. Essentially no back reflections exist for the inventions described and the output profiles are essentially oval with the relatively sharp edges typical of standard, axial fiber output profiles. Both inventions describe embodiments that may be produced with far lower cost fiber optic materials than required by Pon (1.1 CCDR and 1.05 CCDR) but both inventions also suffer the same flaw. Fusion 110 of the bevel tipped 105 fiber 95 to the cap 100, either directly (Brekke, FIG. 5) or through a glass sleeve (Griffin, FIG. 6), results in high residual stresses "frozen" within the assembly that cannot be removed; the fused features of the output are contiguous with heat labile polymers on the transmitting fiber optic conduit such that the assemblies cannot be thermally annealed.

These stresses were problematic at the higher average power settings of lasers in use a decade ago, where repeatedly and rapidly heating and cooling the side firing fiber caps amplified preexisting stresses and/or flaws, often causing fractures at the junctions of fused and un-fused portions of the assemblies. Modern surgical laser powers can deliver twice the average power of the former installed base, making the control of Snell and Fresnel reflections even more important and rendering inviable the solutions taught in '499, '657 and even '699.

Prior art '297 FIG. 7 teaches a side fire optical device for laterally redirecting electromagnetic radiation-comprising: a cap member 150 comprising a closed end section 135, a tube section having a bore 115, and a transmitting surface 145; a sleeve 130 received within the bore of the tube section, the sleeve including a bore 133 and an exterior surface 137 that is fused to a surface of the bore of the cap 138 member; and a fiber optic segment 125 comprising an exterior surface 142 that is fused to a surface of the bore of the sleeve 143, a beveled end surface 140 positioned adjacent the transmitting surface of the cap member and a receiving end 144 opposite the beveled end surface that is within the bore of the tube section, wherein the beveled end surface is angled relative to a longitudinal axis of the fiber optic segment such that electromagnetic radiation propagating along the longitudinal axis of the fiber optic segment is reflected by the beveled end surface at an angle that is transverse to the longitudinal axis and through the transmitting surface of the cap member and variations thereof. Minor Fresnel reflections remain due to the lower refractive index of the fiber optic segment cladding 120 relative to the fiber optic segment core 125 and the sleeve 130 and at the fuses surfaces (due to contamination, captured gases, differential surface chemistry, etc.).

In particular, the fiber optic segment 125 of the prior art illustrated in FIG. 7 must be produced from a very limited selection of standard optical fiber materials unless custom drawn optical fiber is utilized. Standard optical fiber raw materials for constructing the fiber optic segment 125 are produced with buffer coatings and jacket materials. These polymers that must be removed completely, without damaging the exterior surface 142 of the fiber optic segment least gas bubbles form in the fusion process. Custom draws of optical fiber typically require a large minimum order and command premium prices; in the current marketplace, a minimum order custom optical fiber for the prior art '297 would provide sufficient material for approximately 250,000 to 1 million assemblies, sufficient devices for supplying 100% of the US market for 1 to 4 years.

Side fire fibers that are currently available to surgeons are exclusively single use devices that are discarded post-operatively and cost as much as $1300 each. More than one fiber is often required to achieve the surgical goal, particularly in benign prostatic hyperplasia (BPH) cases where the patient has been taking drugs such as Flomax for relief of BPH symptoms, the prostate gland is larger than 30 grams and/or the patient has had a prior prostate resection. The fiber optic conduit and laser connector represent roughly 95% of the materials costs and between 20% and 40% of the labor costs of producing a side fire fiber.

Furthermore, current fiber designs are fixed in output profile and provide no mechanism for altering the size of shape of the output spot without altering the lateral fiber design. This invariable output profile requires surgeons to physically vary the distance between the fibers output surface and the target tissue and/or alter the laser average power to favor vaporization or coagulation. Moreover, the physical ability of the surgeon to comply with this distance variation requirement, while aiming the fiber's output precisely, is often difficult within the confined spaces of intraluminal surgery and while overcoming the fiber's resistance to twist.

For fibers used with wavelengths where water is not strongly absorbing, e.g. in the visible spectrum, it is best practice to hold the fiber apart from the tissue by one to two millimeters to minimize tissue adhesion. At wavelengths where water absorbs strongly, e.g. in the near IR too much laser energy is lost to boiling water if there is any appreciable distance between the fiber and the target tissue so fibers are held in close contact. In either case, a popular technique is sweeping the fiber output in an arc of approximately 50 to 60 degrees while slowly pulling it back toward the scope. Precise control of the limits of the fiber output arc is critical for safe and efficient surgery.

SUMMARY

Before proceeding to descriptions, it may be helpful to define the term "resposable". As used herein, "resposable" means a device within which a component or components, such as a surgical tip patient contact assembly, is optionally disposable and in which one or more other components, such as a transmitting fiber optic conduit for use with the optionally disposable part, is reusable.

One embodiment (FIG. 10) includes a side fire optical device for laterally redirecting electromagnetic radiation in combination with prepared fiber optic conduit where both the fiber conduit and the side fire optical device (or cap) are equipped with a threaded means of decoupling and re-coupling caps from the fibers, representing a rudimentary resposable side fire fiber optic surgical system. A practical deficiency of the embodiment is exposure of the delicate tip of the fiber optic conduit during cap replacement.

Another embodiment (FIG. 22) includes a more refined resposable side fire surgical system wherein the delicate energy delivery tip of the fiber optic conduit can be retracted within a protective sheathe, or cannula, prior to removal and replacement of the patient contacting and disposable portion of the side firing fiber optic surgical system. FIG. 22 also illustrates a third embodiment in combination with the second embodiment—an ergonomic fiber aiming variation that is separately illustrated in FIG. 20—the combination of which illustrates a fourth embodiment.

Yet another embodiment permits operator control of the spot size and divergence of the lateral output of the device is separately illustrated in FIG. 21 and is illustrated in combination with the ergonomic fiber aiming embodiment in FIG. 18 as a sixth embodiment. A seventh embodiment is represented by the combination of the resposable embodiment (depicted in FIG. 22 in combination with the ergonomic output aiming embodiment) in combination instead with the operator focus and divergence control embodiment of FIG. 21. A final embodiment is the combination of all three primary embodiments: free rotation for ergonomic aiming of the lateral output, operator control of output irradiance through spot size and divergence) and safe and validatable reprocessing of the surgical device for reuse through replacement of patient contacting components.

Still another embodiment is a lateral redirecting device that includes a lateral redirecting cap having a one-piece construction consisting of fused quartz and/or fused silica, including a guide section and an open-end section, the open-end section and the guide section divided by a lens, the open-end section including a bore which terminates at the lens, the open-end section shaped to receive a fiber optic cable, the guide section including a light path from the lens to a reflecting surface and then to a transmitting surface, the reflecting surface configured to direct electromagnetic radiation from the lens through the transmitting surface at a side of the tube portion; the lateral redirected cap affixed to a cannula.

Yet still another embodiment is a lateral redirecting device that includes a transmitting optical fiber affixed to a main body; the main body carrying a cannula, wherein the transmitting optical fiber is positioned within the cannula; the cannula carrying a lateral redirecting cap having a lateral output; the transmitting optical fiber having an fiber output face proximal to a lens input carried by the lateral redirecting cap; the lateral redirecting device adapted to rotate the cannula and lateral redirecting cap relative to the main body without rotating the transmitting optical fiber and/or adapted to reduce a fiber-lens separation.

BRIEF DESCRIPTION OF THE FIGURES

For a more complete understanding of the disclosure, reference should be made to the following detailed description and accompanying drawing figures wherein:

FIG. 10 includes magnified side cross-sectional views of a lateral delivery optical device in accordance with embodiments of the invention. FIG. 10A includes a closed end with, preferably a vacuum bubble adjacent to the reflecting surface, FIG. 10B omits the closed end of the tube while maintaining the end within the protective metal tube.

FIG. 11 is a magnified side cross-sectional view of a lateral delivery optical device in accordance with embodiments of the invention. FIG. 11A includes a control device and FIG. 11B includes a lateral delivery optical device used with the control device.

FIG. 14 provides a magnified isometric view (FIG. 14A) of a raw material component (FIG. 12) processed for producing embodiments of the invention and a magnified top view (FIG. 14B) of an alternatively processed component (FIG. 12) for producing embodiments of the invention.

FIG. 15 is a magnified isometric view of one step for producing embodiments of the invention.

FIG. 17 presents three orthogonal cross-sections of a multi-fiber variant of a preferred embodiment. FIG. 17A is a horizontal cross-section; FIG. 17B and FIG. 17C are longitudinal cross-sections.

FIG. 19A and FIG. 19B presents two cartoons depicting the collimated (FIG. 19A) and diverging (FIG. 19B) outputs of the focus control embodiment of the invention.

FIG. 20A is the device (less laser connector) in cross-section and FIG. 20B is an exploded isometric representation of the same.

FIG. 22 illustrates a resposable embodiment of the invention where the cross-sectional depiction in 22A is the device as situated in surgical use, 22B is the same cross-section where the fiber has been retracted for safe replacement of the cap/cannula/plug subassembly, 22C illustrated the replaceable subassembly detached from the reusable assembly with the fiber in the safe, retracted position and 22D presents detail of the fiber working tip FIG. 23 illustrates a disposable patient contacting assembly that may be removed and replaced interoperatively for significant cost reduction.

Figure 1:
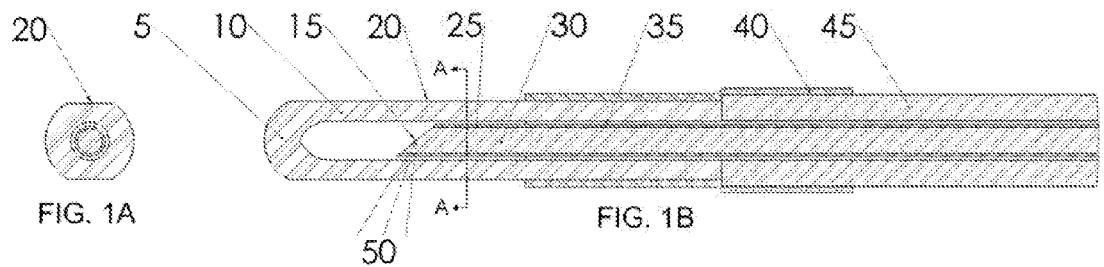
FIG. 1 is orthogonal, magnified side cross-sections (FIG. 1A and FIG. 1B) illustrating the essential features of prior art (adapted from Abe, et al.).
Figure 2:
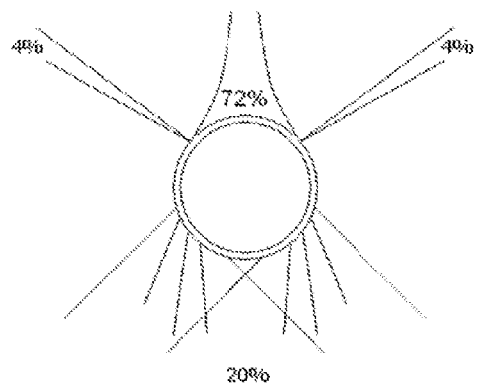
FIG. 2 is a magnified cartoon illustrating the variety of off-axis angles for misdirected rays, and the primary (desired) output for side fire fiber optic devices in prior art (adapted from Pon).
Figure 3:
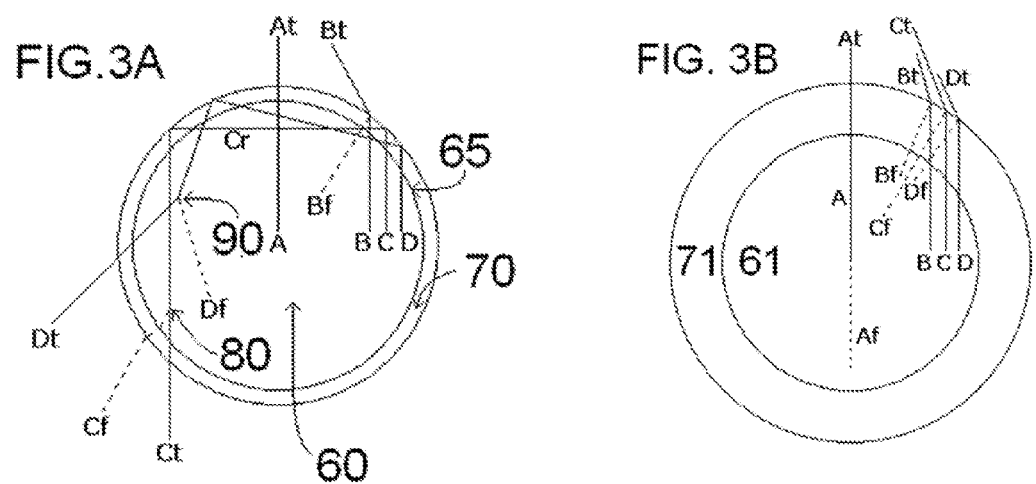
FIG. 3 are magnified cross-sectional cartoons depicting the various fates for rays of light within early prior art (FIG. 3A) and subsequent prior art (FIG. 3B) side fire fiber devices (adapted from Pon).
Figure 4:
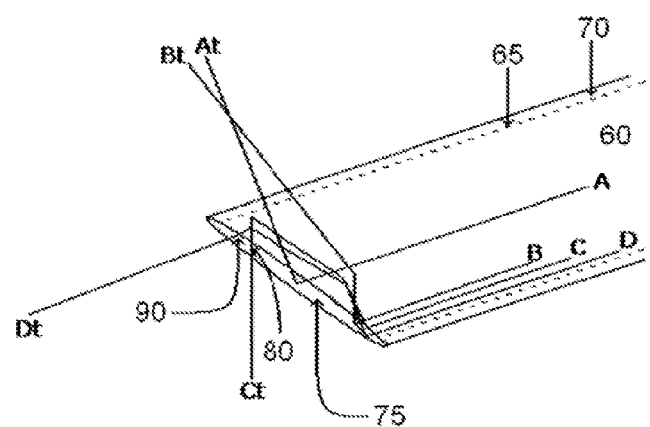
FIG. 4 is a magnified isometric cartoon of the reflecting tip of the lateral delivery optical device of FIG. 1 and FIG. 3A, providing another view of the fates for rays of light within prior art devices (adapted from Pon).
Figure 5:
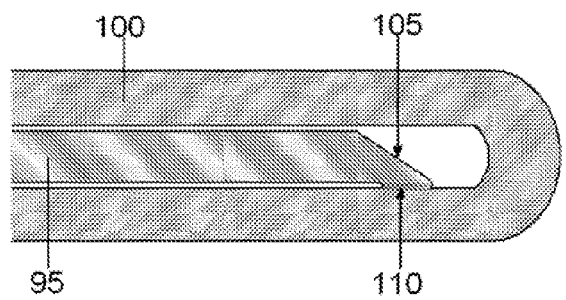
FIG. 5 is a magnified side cross-section view of prior art (adapted from Brekke).

While specific embodiments are illustrated in the figures, with the understanding that the disclosure is intended to be illustrative, these embodiments are not intended to limit the invention described and illustrated herein.

DETAILED DESCRIPTION

The herein provided embodiments include a side fire optical device ("cap") for redirecting electromagnetic radiation, methods of their manufacture, and methods of their use, particularly in combination with, and coupled to, transmitting fiber optics. These embodiments minimize potential Fresnel reflections at fused surfaces and eliminate Snell and Fresnel reflections in a self-contained lateral output assembly (within which a transmitting optical fiber conduit may be subsequently attached), the construction of which involved lower cost raw materials and fewer manufacturing steps; provide a side fire fiber where the protective cap can be replaced interoperatively and even intraoperatively; and provide mechanisms and processes for altering the size or shape of the output spot without altering the lateral fiber design.

The invention claimed and described herein includes a strategy for forming optical fiber caps for lateral redirection of laser light or light for spectroscopy and various assemblies thereof. In a preferred embodiment, a optically polished surface for redirecting electromagnetic energy in accordance with Snell's Law (a bevel surface) is produced upon a short cylinder of uncoated (unclad) and optically transparent material (where in prior art this surface is produced upon an optical fiber or segment of optical fiber) that is fused within a tiny test-tube of the same material, near the closed end, producing an enclosed space of air or partial vacuum between the bevel surface and the closed end of the tube while retaining most of the open bore of the test tube: a lateral cap device for redirecting electromagnetic radiation (e.g., FIG. 8).

A transmitting fiber optic conduit, equipped on one end for coupling to a light source, typically a laser, and the other end equipped with a flat polished output ("laser fiber"), may be inserted within the open bore of the lateral cap to produce a side fire fiber with utility in laser surgery, ordinance ignition and spectroscopy.

Alternatively, the short cylinder of uncoated optical material may be equipped with a lens for coupling the output of laser fiber and the laser fiber may be similarly equipped with a lens-end or other optical treatments such as tapers for coupling to the lateral cap. Lenses within the lateral cap structure may be cylindrical, hemispherical, spherical sections, aspheric or meniscus lenses.

Embodiments of the invention include addition of a hollow metallic shroud surrounding the lateral cap, equipped with an output window for the redirected light from the lateral cap, and secured to the optical fiber buffer coating (sometimes called "jacket") for protection of the lateral cap element. Unlike prior art side fire fibers with the delicate bevel tipped optical fibers, providing a means for replacing caps that wear out in use is greatly simplified where the laser fiber tip is relatively rugged: flat polished or lens-ended. Modifications of the metallic shroud to permit reversible coupling between a section that is secured about the lateral cap and a section secured to the laser fiber buffer enable the lateral cap to be easily replaced.

Further embodiments of the invention are enabled by extending the metallic shroud segment, unattached to the fiber buffer, to a control device located some distance along the laser fiber where it is affixed to one half of the control device, where the other half of the control device is affixed to the fiber buffer, enabling adjustment of the distance between the laser fiber output and the lateral cap input for external control of the delivered lateral spot size.

Among the objects of the present invention are the following:

To provide a new and useful method of producing self-contained lateral cap devices for redirecting electromagnetic radiation when attached to laser fibers, at angles roughly orthogonal to the original axial output;

To provide a new and useful construct for redirecting electromagnetic radiation when attached to laser fibers, at angles roughly orthogonal to the original axial output where reflections and distortions of the output are essentially eliminated;

To provide a new and useful construct for redirecting electromagnetic radiation when attached to laser fibers where a variety of beam shaping elements may be exploited, within the lateral cap design and for the laser fiber coupling to the lateral cap;

To provide a new and useful construct for redirecting electromagnetic radiation when attached to laser fibers where the lateral cap may be replaced during a surgical session and/or between surgical sessions; and To provide a new and useful construct for redirecting electromagnetic radiation when attached to laser fibers where the lateral output characteristics may be altered during surgery without the need to remove the fiber from the endoscopic device.

The novel features that are considered characteristic of the invention are set forth with particularity in the appended claims. The invention itself, however, both as to its structure and its operation together with the additional objects and advantages thereof will best be understood from the following description of the preferred embodiments of the present invention. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the description of the invention is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

Figure 8:
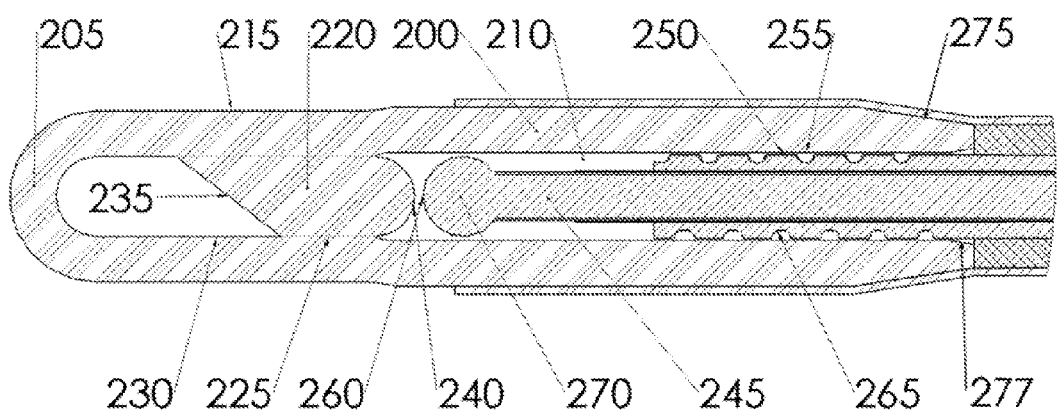
FIG. 8 is a magnified side cross-sectional view of a lateral delivery optical device in accordance with embodiments of the invention.

Embodiments of the present invention FIG. 8 are directed to a laser energy delivery device for laterally redirecting electromagnetic radiation comprising: a cap member 200 comprising a closed end section 205, a tube section having a bore 210, and a transmitting surface 215; and a solid cylindrical segment 220 comprising an exterior surface 225 that is fused to a surface of the bore of the cap 230, a beveled end surface 235 positioned adjacent the transmitting surface of the cap member and a receiving end 240 opposite the beveled end surface, wherein the beveled end surface is angled relative to a longitudinal axis of the fiber optic segment such that electromagnetic radiation propagating along the longitudinal axis of the fiber optic segment is reflected by the beveled end surface at an angle that is transverse to the longitudinal axis and through the transmitting surface of the cap. The receiving end of the solid cylinder that partially fills the cap bore may be a flat mating surface for coupling a fiber optic segment or it may be curved or sculpted to act as a lens 240 for shaping and receiving the transmission of the fiber optic conduit 245 delivering energy to the cap device. The fiber optic conduit comprises an exterior surface 250 that may be equipped with grooves or pits 265 for adhesion to the surface of the open bore of the cap 255 and positioned in contact with or nearly in contact with the flat or curved end of the solid cylinder 240 and the fiber optic conduit's transmitting surface may be flat, curved or shaped 260 to modify the output profile. The beveled end surface is angled relative to a longitudinal axis of the solid cylinder (and thus, the fiber optic conduit) such that electromagnetic radiation propagating along the longitudinal axis of the solid cylinder is reflected by the beveled end surface at an angle that is transverse to the longitudinal axis and through the transmitting surface of the cap member 215.

Unlike the invention described in prior art '297, the current invention utilizes low cost and readily available fused quartz (or fused silica) rod stock for producing the solid cylindrical element and does not utilize an intermediate sleeve element. The elimination of the sleeve element 130, utilized in the prior art, affords greater space 210 within the cap bore, enabling the use of a transmitting optical fiber conduit equipped with a ball lens 270 or an up-tapered fiber for altering the characteristics of the light delivered to the solid cylindrical element 220. Flexibility in employing myriad transmitting optical fiber conduit designs permits greater control of the output spot profile relative to prior art, without altering the optical design of the invention: the lateral cap device.

More importantly, replacing the fiber segment of prior art '297 (having a core with a refractive index of 1.457 (fused silica) that is surrounded by a fluorine-doped cladding with a lower refractive index of 1.44 (NA=0.22) with the solid cylindrical element was found to significantly reduce the reflected component of the light exiting the fiber by way of reflection from the beveled planar face. Notably, the Fresnel reflections in '297 become large within the outer 3% of the fiber core, e.g. almost 3% for rays at exiting at 97% of the fiber core radius, almost 10% at 98% of the radius or almost 25% at 98.5% of the radius, and become total internal reflections for the outer ~1.2% of the core.

The total reflected energy due to the light transitioning the cladding in the '297 patent is approximately 2% greater than that of the herein presented invention, absent the cladding interface. While 2% is a relatively small improvement, any energy not directed to doing surgical work causes structural damage to the device, for example by raising the fiber tip (cap) temperature and facilitating tissue adhesion. Further, in that the reflections that are eliminated emanate from a well-defined geometric portion of the prior art, that energy is far less diffuse than the bulk of other reflections that are eliminated in '297, and is therefore far more problematic. A truly efficient fiber, such as disclosed herein, can remain cool and avoid thermal damage to both the fiber and surrounding tissues during use (e.g., during surgical use).

Another example of the invention, FIG. 10, includes the assembled lateral delivery cap member 300 is housed within a protective metal tube 310 that is closed on one end 320, or partially closed, and equipped with an opening 333 within the cylindrical wall that is positioned adjacent to the transmitting surface 340. A male threaded portion of a metal crimp section 330 can be secured by crimping 350 (or other means) to the outer polymer coating (buffer) 345 of the optical fiber conduit 355 in addition to securing the roughened or grooved portion of the optical fiber buffer 305/325 within the open bore 315 of the transmissive protective cap with adhesive around 325. The male threaded crimp section mates within the female threaded section 360 at the open-end of the protective metal tube covering the lateral delivery cap. FIG. 10 also illustrates the use of an up-tapered fiber 370 for delivering optical energy of reduced divergence to the receiving face 365 of the lateral fiber cap.

An alternative embodiment, illustrating the basic principles for providing a resposable side fire fiber is also illustrated by FIG. 10. The side fire optical device includes a glass tube portion 300 having a one-piece construction, including a guide section and an open-end section, the open-end section and the guide section divided by a lens 365, the open-end section including a bore 315 which terminates at the lens 365, the open-end section shaped to receive a prepared terminus of a fiber optic cable 370. The glass tube portion 300 is protected by a metallic envelope 310, also closed 320 or partially closed on one end and equipped with a threaded 360 proximal section. Energy emitted from fiber optic terminus 370—in this case an up tapered fiber segment for reducing divergence—couples to the one-piece lateral delivery cap 300 through the lens 365 and is redirected by the TIR bevel surface 343, through the transmitting surface 340 at the opening 333 in the metallic cap 310.

A metallic crimp sleeve 350 is equipped with a threaded stub 330 and is crimped onto the outer diameter at the ETFE buffer 345 of the transmitting fiber optic conduit 355. For an embodiment offering a capacity for replacing the consumable portion of the device, consisting of the one-piece lateral redirection element 300 within the surrounding metallic cap 310, the fiber buffer 345 need not be equipped with a helical groove 325/305 for enhanced adhesion within the glass cap bore 315, but chamfering of the ETFE terminus at 375 may be warranted to aid in insertion. In rotating the outer metal cap 310/360 about the fiber metal sleeve 350/330, the consumable portion of the device may be separated from the reusable portion of the device (consisting of the transmitting fiber optic conduit 355/345/370 and metal crimp sleeve 330/350, typically a torque controller and the laser connector. Where sufficient care is taken to prevent damage or contamination to the fiber conduit terminus 370, a replacement cap assembly may be reattached.

Still another example, FIG. 11, includes an extension cannula 440 coupled to the metal protective cap 450 by way of a threaded coupler 430 within the bore 400 of the metal protective cap and the bore 410 of the extension cannula, with the extension cannula extending a length of the transmitting optical fiber conduit 405 sufficient to traverse the length of the working channel within a cystoscope. The proximal end of the extension cannula 415, outside of the cystoscope port, is affixed to one half 420 of a control device. Unlike the examples depicted in FIGS. 8 and 10, the buffer 400 of the delivery end of the transmitting fiber optic conduit is not equipped with grooves and is not adhered to the inside wall 425 of the glass cap bore such that the female threads 435 of the threaded coupler 430, in concert with the male threaded portion 445 of the metal crimp section 455, provide a means of adjusting the gap between the transmitting face 460 of the up-tapered fiber optic conduit 465 and the receiving face 470 of the solid cylindrical element 475 fused within the glass protective cap 480 via rotation of the transmitting optical fiber conduit 405 affixed within the second half 485 of the control device situated outside of the cystoscope working channel port. Through rotating one half of the control device, relative to the other half, the gap separating the transmitting face of the fiber optic conduit 460 and the receiving face of the fused lateral cap assembly 470 may be narrowed or widened, altering the lateral output spot size at the glass cap transmitting surface 490. Alternatively, the threads of the threaded coupler and the threads of the metal crimp section may be removed and the adjustment mechanism, such as threads, provided within the control device.

Figure 9:
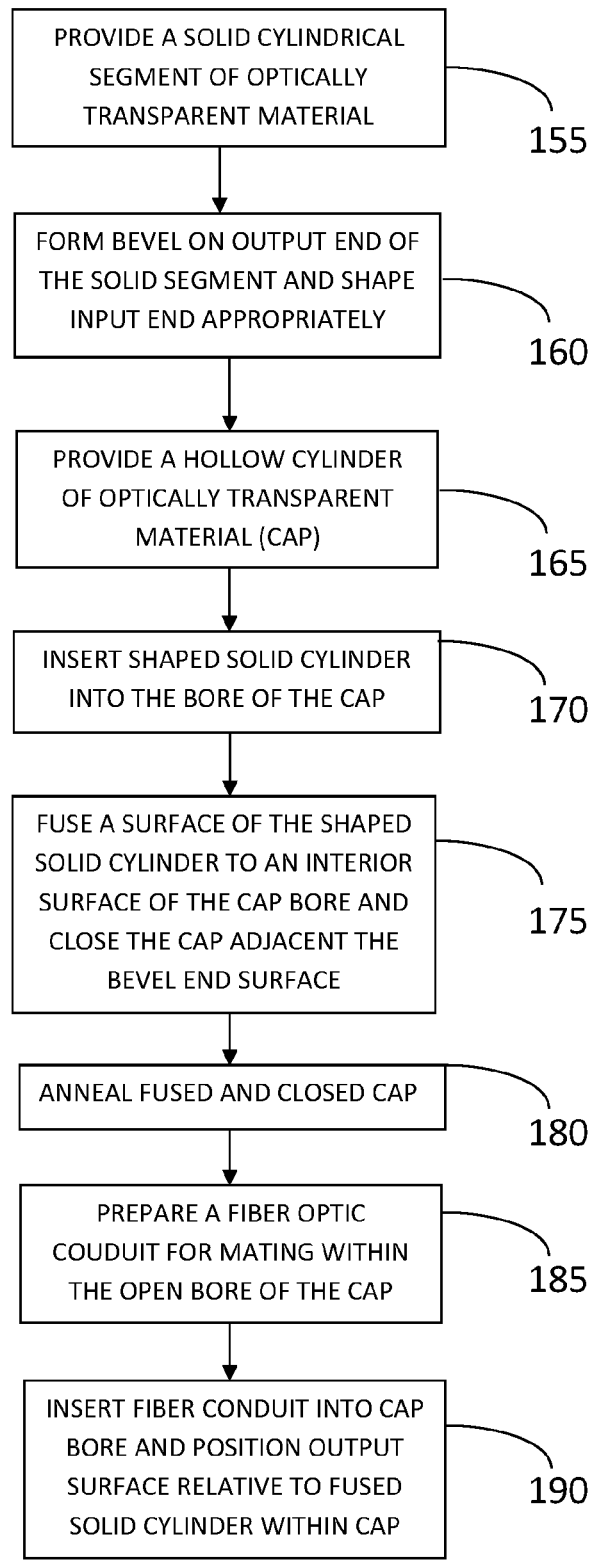
FIG. 9 is a flowchart depicting the essential steps required to produce embodiments of the invention.
Figure 12:
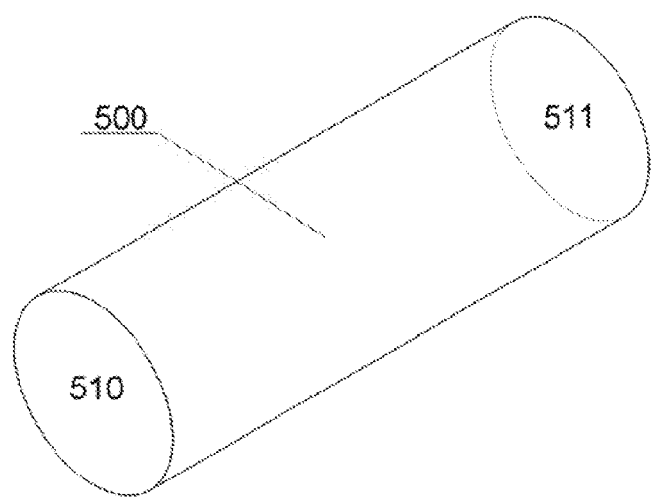
FIG. 12 is a magnified isometric view of a raw material component for producing all embodiments of the invention.
Figure 13:
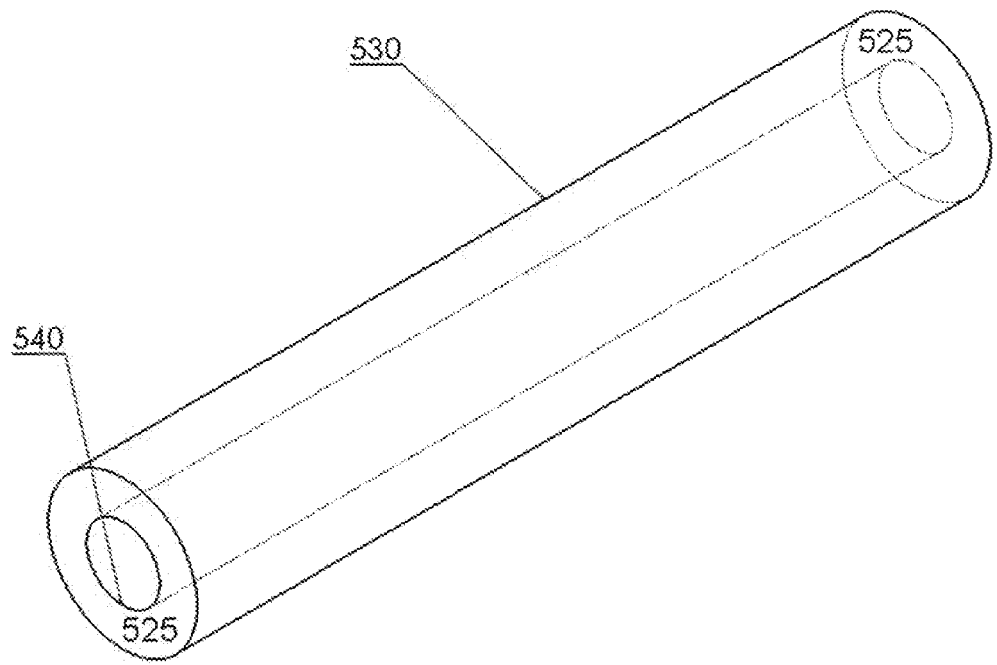
FIG. 13 is a magnified isometric view of a raw material component for producing all embodiments of the invention.

Another embodiment of the herein presented invention is a method of manufacturing the lateral cap device. In one example, FIG. 9 depicts five manufacturing steps 155-175 to produce the lateral cap device and subsequent steps 180-190 for producing a basic surgical device. FIG. 9 is a flowchart illustrating steps for manufacturing embodiments of a lateral delivery cap optical device described above. Initially, at steps 155 and 165, a solid cylindrical, transparent segment (FIG. 12), having a cylindrical surface 500 and two planar surfaces 510 and 511 and a hollow cylindrical, transparent segment—the cap element—(FIG. 13), having an outer cylindrical surface 530, an inner cylindrical surface 540 and two planar surfaces 525 are provided, preferably made of fused quartz (and preferably electrically fused quartz) or fused synthetic silica. The solid cylindrical segment (FIG. 12) and the cap precursor (FIG. 13) can be formed in accordance with any of the embodiments described above. Initially, the solid cylindrical segment is a straight section of rod, as shown in FIG. 12. In one embodiment FIG. 14A, the receiving end 511 of the solid cylindrical element remains a flat, optically polished surface. In another embodiment FIG. 14B, the receiving end 512 of the solid cylindrical element is either formed into a lens or a lens is attached to the receiving end 512, illustrated as a cylindrical lens in FIG. 14B. The lens formed or attached to the solid cylindrical element may be a cylindrical lens in any orientation, a hemispherical lens or partial spherical lens, a meniscus lens or aspheric lens.

At step 160 a beveled optical surface 550 (FIGS. 14A and 14B) can be formed at the reflection end 510 (FIG. 12) of the solid cylindrical element such that the angle of the bevel lies at the critical angle for the worst case ray of light delivered to the bevel surface, through the receiving surface 511, regardless of treatments to the receiving surface, e.g. 240 in FIG. 8, or the delivery surface 260 in FIG. 8 or numerical aperture reduction by way of tapering 370 in FIG. 10 within of the transmitting optical fiber conduit 355, such that all light rays imparting the bevel surface 550 (FIGS. 14A and 14B) will be totally reflected in a lateral direction relative to the axis of the transmitting optical fiber conduit. In one embodiment of the cap member, a chamfer 277 (FIG. 8) is formed at the optical fiber conduit receiving end to form a chamfered opening to the open bore 255 and/or a chamfer 275 is formed on the outer diameter of the cap member.

At step 170, the shaped solid cylindrical element 555 is inserted into the bore 560 of the cap element 565, near the planar face 570, as shown in FIG. 15. At step 175 (FIG. 16), an exterior and cylindrical surface 600 of the shaped solid cylindrical element 605 is fused to an interior surface 610 of the bore 615. The fusion of the shaped solid cylindrical element 605 to the cap 625 may be accomplished using conventional techniques. In one such technique, the shaped solid cylindrical element 605 and the cap 625 are rotated under laser illumination. The laser is scanned down the cap 625 from position 630 to 640, slightly shrinking the bore 615 until fusion is accomplished and the cap is closed 650. Alternative techniques to fuse the shaped solid cylindrical element 605 to the cap 625 include furnace fusion, flame fusion, low temperature glass melt and other conventional techniques. Laser and/or flame fusion techniques are preferred, enabling, for example, fusion and closing of the cap in a single production step.

Figure 6:
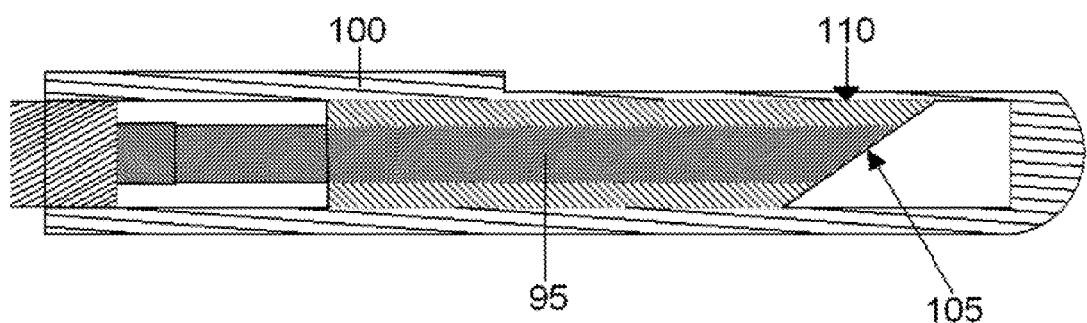
FIG. 6 is a magnified side cross-section view of prior art (adapted from Griffin).
Figure 7:
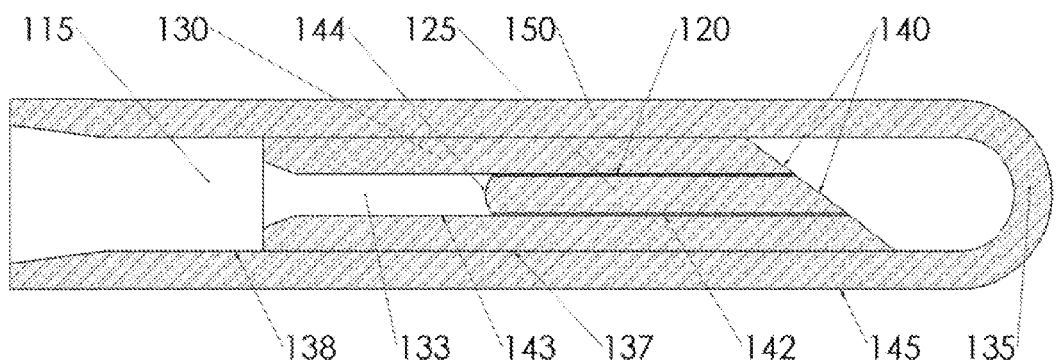
FIG. 7 is a magnified side cross-section view of prior art (adapted from Griffin).

For applications where the operating medium is of low refractive index, e.g. in air, or where the optical output of the lateral optical device may serve as input to a second, similar device, e.g. absorption spectroscopy probe, it may be desirable to produce a flat transmissive surface upon the cap cylindrical outer diameter, similar to that depicted in FIG. 6.

Figure 16:
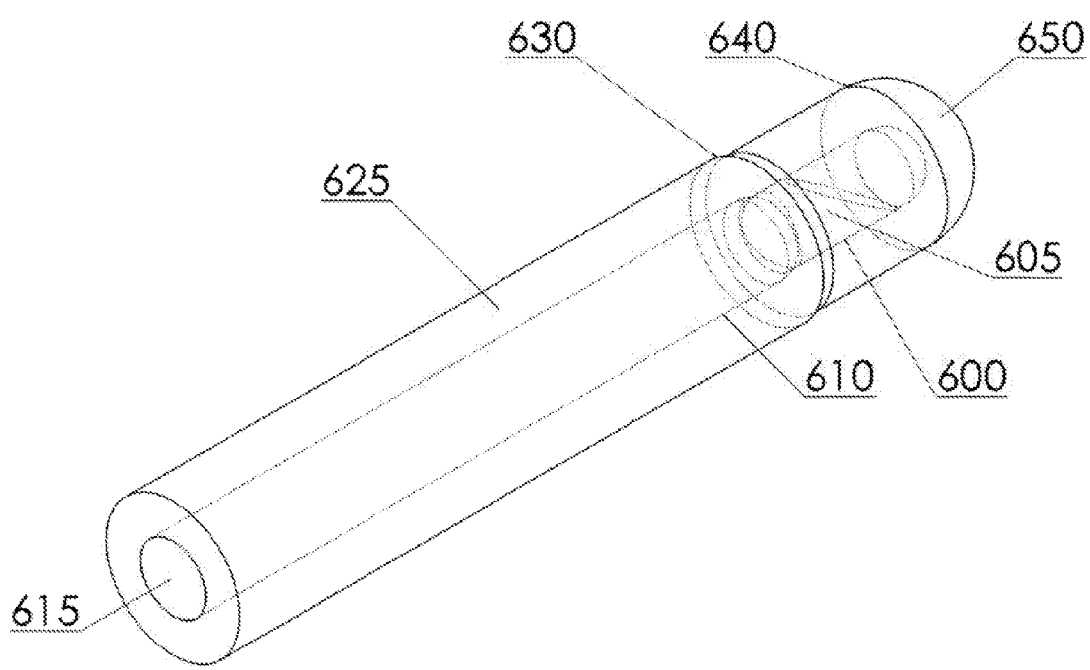
FIG. 16 is a magnified isometric view depicting the essential elements of the invention.

In accordance with embodiments of the method, at step 180 the assembled lateral optical device FIG. 16 is annealed at a temperature in excess of 1100° C. This process relieves the stresses formed in the components of the lateral optical device FIG. 16 due to the polishing, beveling, fusion and cap closing processes as well as optional processes such as lens formation, lens attachment and chamfering for example. Once annealed, the lateral optical device becomes more capable of withstanding the redirecting of high powered electromagnetic radiation and far more capable of withstanding the rapid thermal cycling inherent in surgical use as compared to prior art electromagnetic radiation redirecting devices.

In another embodiment as depicted in FIG. 17, a device 690 for redirecting electromagnetic energy may employ a fiber optic bundle 700 containing discrete fiber optic strands 710 that may be coupled to one of more laser energy sources, imaging systems and/or analytical instrumentation, thereby permitting multiple functions within a single device. In one example, a single fiber optic 710 may carry a surgical wavelength of laser light that is suitable to, for example, vaporize and/or fragment kidney stones while another fiber optic 710 transmits laser light having a surgical wavelength that is suitable for coagulation. In another example, one of the fiber optics 710 can carry laser light having a wavelength that is suitable for diffuse reflectance while one or more of the other fiber optics 710 are used to collect the reflectance for spectral analysis. As a result, the device 690 can be used to both analyze the tissues of the patient and treat those tissues without having to change devices. Thus, the device 690 can be configured to have one or more fiber optics 710 that can be used to provide optical screening for one or more cancers or other diseases and other fiber optics 710 that are configured to perform surgery.

In still another example, the device 690 may be used to locate and treat vulnerable plaque (a semi-fluid inclusion in the arterial wall that causes fatal heart attacks when it escapes) in coronary arteries. Here, one or more of the optical fibers 710 are connected to a rapidly tunable visible laser (e.g., 200 nm scan range). The laser light is delivered from an emission fiber to the arterial wall through the device 690, which redirects the light to an arterial wall, which it penetrates. When it encounters vulnerable plaque the scattered laser light is altered in a manner that is detectable when delivered to a spectrometer by the surrounding fiber optics 710 (e.g., detection optical fiber) of the device 690. If more than one ring of fibers 710 is used to collect the scattered light, different depths can be scanned, giving a low resolution "image" of the plaque profile. While this alone is of great value, one may also use other fiber optics 710 of the bundle 700 to deliver a surgical wavelength of laser light that can "cook" the vulnerable plaque and make it a solid material that cannot escape through the artery wall.

In still yet another example, one of the fiber optics 710 of the device 690 can be used to deliver Raman excitation (e.g., via an emission optical fiber) while a different optical fiber 710 of the bundle 700 collects the florescence from prostate tissue. If the returned spectrum (e.g., via a detection optical fiber) indicates cancerous tissue, other fiber optics 710 of the fiber optic bundle 700 that are not being used for spectroscopy can deliver surgical wavelengths of laser light to kill the cancerous tissue. As a result, the device 690 can be used to provide real-time targeting of deceased tissue while sparing healthy tissue.

In yet another example, each of the fiber optic element 710 in the bundle 700 can be connected to a high energy pulse Nd:YAG laser and each of the seven Nd:YAG lasers feeds a similar bundle of seven fibers connecting to seven devices 690. Accordingly, each device 690 is fed by seven Nd:YAG lasers and each Nd:YAG laser supplies a portion of its energy pulse to each of the seven devices 690. Such an arrangement would have utility as a highly redundant laser ordinance ignition system for seven separate charges. For any single charge to fail to ignite, all seven Nd:YAG lasers must fail.

As in other kinds of collateral damage, unintended tissue damage in laser BPH surgery results from too much energy being applied to a target with inadequate precision, a consequence of the low optical performance of existing lateral fiber energy delivery systems and difficulty in precisely "aiming" the fiber output; urological surgeons must apply considerable torsional force when aiming the output of a side-fire fiber, the opposite end of which is secured to the laser generator. Overcoming the fiber's resistance to being twisted becomes increasingly fatiguing in protracted surgical sessions and fibers may slip within the torque control devices supplied for aiming the output beam. Because the lateral redirection functionality of the disclosed invention is decoupled from the energy transmission, rotating the output of the fiber to address targets at differing orientations about the prostatic urethra may be accomplished without any need to overcome the fiber's inherent resistance to torsional forces.

This design element may be exploited to provide an ergonomically superior device, a device where no circumferential orientation of the output beam is favored above any other, the importance for which increases with increasing fiber diameters and protracted surgeries. An additional consequence of decoupling the torque or aim control device from the transmitting fiber is that the mechanism for securing the transmitting fiber within the control device need not be as rigorous as in prior art designs. As a result of the need to secure fibers against torsional forces, the pin vises that are commonly used to secure control devices to the fiber's polymer jacket consequently apply considerable and concentrated compressive force to the fiber coating, cladding and core. Such forces are known in the art to result in localized optical losses due to microbending and can lead to catastrophic fiber failure where high energy densities are carried and the source beam output quality is substantially greater than $M^2=1$.

Figure 18:
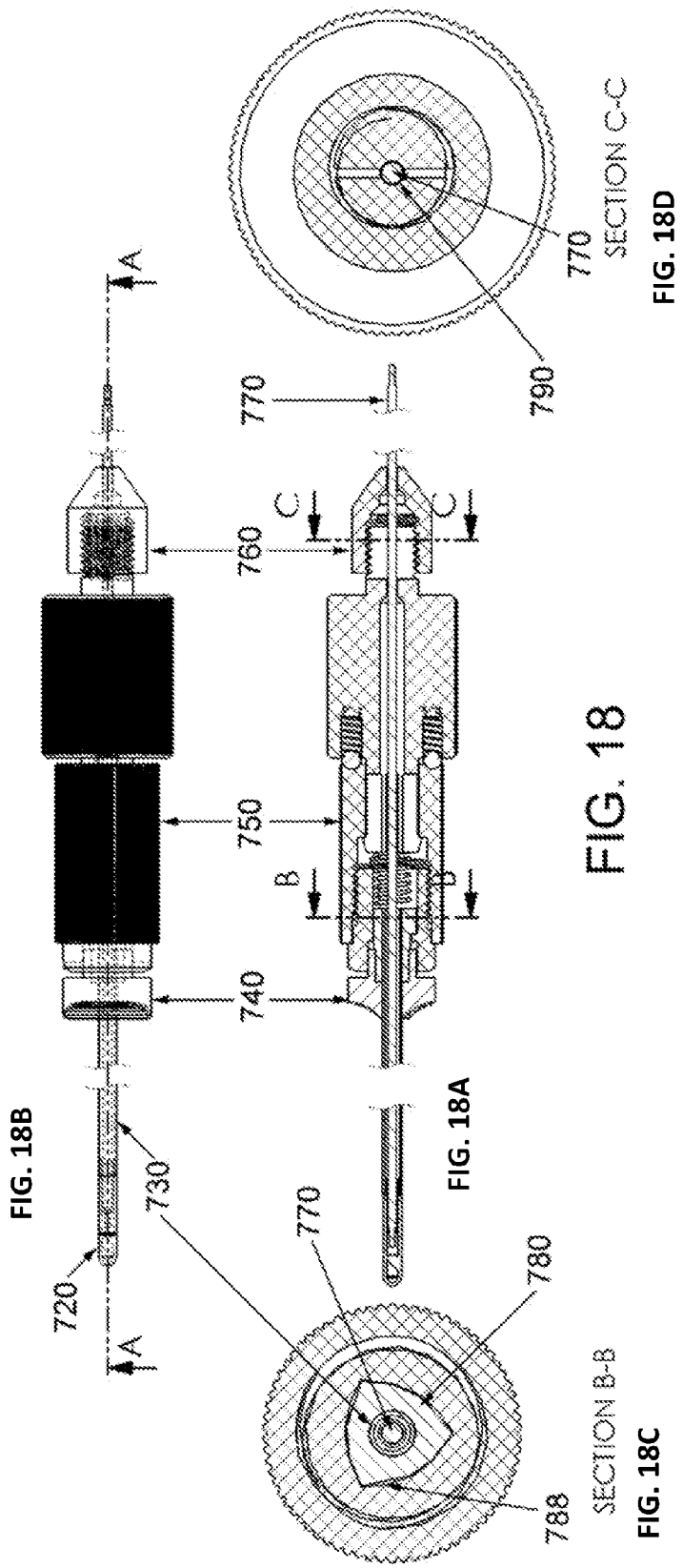
FIG. 18A provides a cross-section of the free cap rotation (fiber output orientation) and focus control combined device depicted in FIG. 18B, with magnified orthogonal cross-section for design detail, as installed on a preferred embodiment of the invention that permits these features.
FIG. 18C shows orthogonal cross-section detail for the keyed indexing element and FIG. 18D shows the orthogonal cross-section detail for the pin vise.

FIG. 18 illustrates two embodiments of the invention in combination, where the transmitting fiber cable 770 is not fixed within the lateral redirecting cap 720, but rather the cap 720 is attached to a stiff tube or cannula 730, within which the transmitting fiber cable 770 is carried and is free to rotate. The cannula can be a hollow tube or rod and composed of, for example, stainless steel, polysulfone, polyethersulfone, polycarbonate, polyacrylate (e.g., polymethylmethacrylate), polyamide, a polyester resin, polyaryletherketone, poly-p-xylene, or acetal resin. The proximal terminus of the cannula 730 is attached to a keyed indexing element 780 that is carried within the fiber rotation control element 750. The transmitting fiber 770 passes through the keyed indexing element 780, the rotation control element 750 and is affixed within the main control body at the pin vise grip 760 at 790. The rotation control element 750 rides on spring-loaded ball bearings to provide high resolution, click-stop angular (rotational) positioning of the device output beam without delivering torsional force to the transmitting fiber 770.

Small arteries are regularly severed when vaporizing bulk tissue with concentrated laser energy. In the majority of cases the arteries are cauterized by the heat in the immediate area of the surgical incision, but in some cases the artery remains open, bleeding into the irrigated surgical field. A critical goal in all surgeries is minimization of blood loss and too much opaque blood within the surgical field may interfere with the surgeon's ability to visualize anatomical landmarks. When bleeders occur, surgeons typically stop vaporization and reset the laser to a lower power to coagulate the artery and then resume vaporization at high power. In that the laser cannot be sterilized and is located outside of the sterile surgical field, this commonly repeated process requires communication with surgical staff, positioned by the laser for this purpose, can significantly extend the length of the surgical session and risks errors due to miscommunication.

The second embodiment illustrated in FIG. 18 addresses the need for lower energy density to coagulate bleeding arteries encountered during surgery by enabling adjustment of the divergence of the output, at or near the protective cap transmitting surface 880 (FIG. 19), through a slight movement of the lateral cap 720 relative to the transmitting fiber output face (800 in FIG. 19) by way of a spring-loaded focus control button 740. Pulling on the focus control button 740 (against a spring), within which the cap-terminated cannula 730 is attached, narrows the gap between the fiber output face and the one-piece lateral cap input, modifying the position of the focal waist and the divergence of the lateral output at the transmissive output surface. The mechanism for adjusting the transmitting fiber output face separation from the one-piece cap input face is not meant to be limiting as those familiar with the art will recognize that there are myriad alternative methods for providing the adjustment for the same purposes as described.

FIG. 19 illustrates this effect of focus control within the lateral redirecting cap 830. FIG. 19A illustrates the default, focused or minimally divergent output for vaporization where the transmitting fiber 870 output face 800 is positioned such that the axial output divergence 810 fills the bulk (80% to 90%) of the lens input 840 aperture, focusing the lateral output 820 beyond the cap transmissive output surface 880. When the focus control button (740 in FIG. 18) is depressed FIG. 19B, the fiber-lens separation (850 in FIG. 19A) between the fiber output face 890 and the lens input face 900 of the lateral cap 830 is reduced 910 (a reduced fiber-lens separation), minimizing the focal effect of the lens element and thereby producing a divergent output 860. The smaller fiber-lens separation 910 reduces the axial output divergence which than fills less than about 80%, 70%, or 60% of the lens input 900 aperture.

In another embodiment, focus control within the lateral redirecting cap can be achieved by increasing the fiber-lens separation. In one instance, the default position for the transmitting fiber output face is positioned such that the axial output divergence fills less than about 80%, 70%, or 60% of the lens input aperture; therefore producing, as a default, a divergent output. In this instance, the extension of the focus control button away from the main body, affects the axial output divergence which fills the bulk (80% to 90%) of the lens input aperture, and focuses the lateral output beyond the cap transmissive output surface.

In bench tests of the focal control embodiment, an approximately 0.5 mm to 1 mm axial dislocation of the fiber input face, closer to the input of the lens element of the one-piece cap, produced an output spot more than three times larger than the focused condition at 2 mm from the caps transmissive surface, in air. A continuum of output spot diameters was observed between the extremes. The spot diameter at the face of the transmissive surface is also changed by approximately 1.5-fold under focus control, offering a means of providing the same irradiance at 100 watts as in produced at 200 watts for tissue contact applications, depending upon the setting used. Those skilled in the art will recognize simple modifications to the focus control device for providing two or more fixed settings as opposed to a default and override arrangement as depicted herein.

Figure 20:
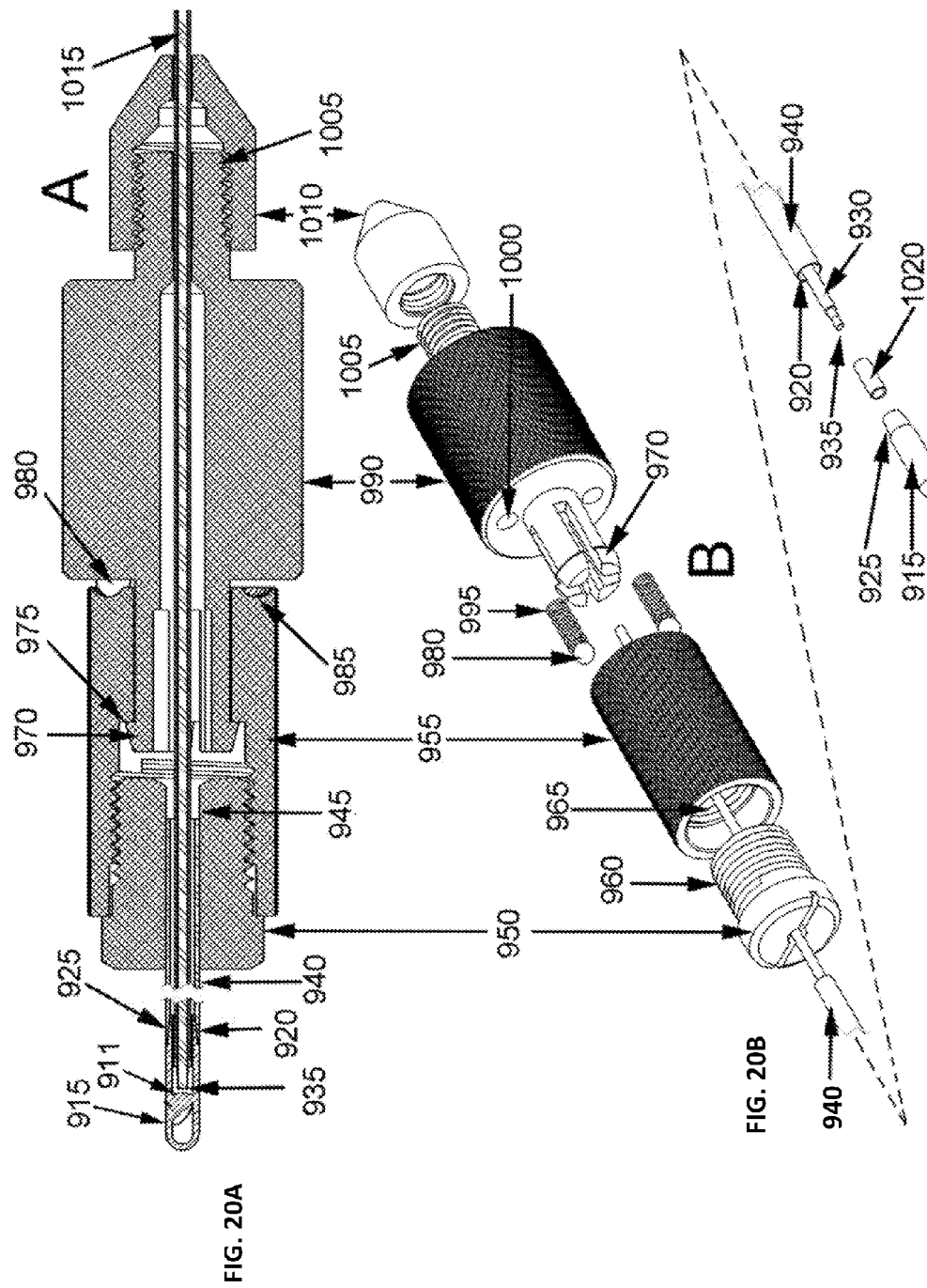
FIG. 20 depicts a free cap rotation only embodiment of the invention where

FIG. 20 is offered for clarity, describing the free cap rotation embodiment separately from the combined rotation and focus embodiment depicted in FIG. 18. Specifically, the transmitting fiber 1015 output face 935 is fixed in position relative to the lateral redirecting cap 915 input face 911 within the pin vise jaws 1005 by securing the pin vise cap 1010. The lateral redirecting cap 915 is step-chamfered 925 at the open end for hermetic mating with an internal chamfer 920 on the end of the torque transferring cannula 940 (or semi-rigid tube), the opposite end of which is secured within the threaded plug 950 within which bore 945 the cannula terminates. The fiber distal end 930 is centered within the lateral redirecting cap 915 through a centering sleeve 1020 that is adhered to the fiber buffer outer diameter 930 but not to the cap inner diameter. (Alternatively, the centering sleeve 1020 may be adhered to the inner wall of the lateral redirecting cap if it is not adhered to the fiber buffer outer diameter 930, as depicted in the resposable embodiment of FIG. 22.)

The rotation control element 955 of the rotation device accepts the threaded plug 950 by means of the plug threads 960 and rotation control threads 965 and is secured within the main body 990 by way of an expanding barb 970 that seats upon an interior shelf 975 within the rotation control element 995. Those skilled in the art will recognize alternative means of securing the threaded plug 950 within the rotation control element 955 such as solvent or thermal fusion, adhesive, etc. and for securing the rotation control element 995 within the main body 990 while providing for rotation.

The position of the rotation control element 955 relative to the main body 990 is such that two ball bearings 980 are captured within a fluted annular groove 985 at the base of the control segment and compress two springs 995 within two holes 1000 in the main body 990. Rotation of the rotation control element 955 relative to the main body 990 produces a ratchet-like feedback to the operator and the springs 995 compressive forces are selected to enable purposeful rotation but for avoiding inadvertent rotation. With the fiber 1015 affixed to the main body 990 and the threaded plug 950 affixed within the rotation control element 955, rotation of the control element 955 relative to the main body 990 rotates the threaded plug 950, rotating the cannula 940 and the lateral redirecting cap 915 but does not rotate the fiber 1015. In that the lateral redirection is affected by the cap 915 and not the fiber 1015, the direction of output of the device rotates with the rotation of the control element 955, without requiring rotation of the fiber 1015.

Figure 21:
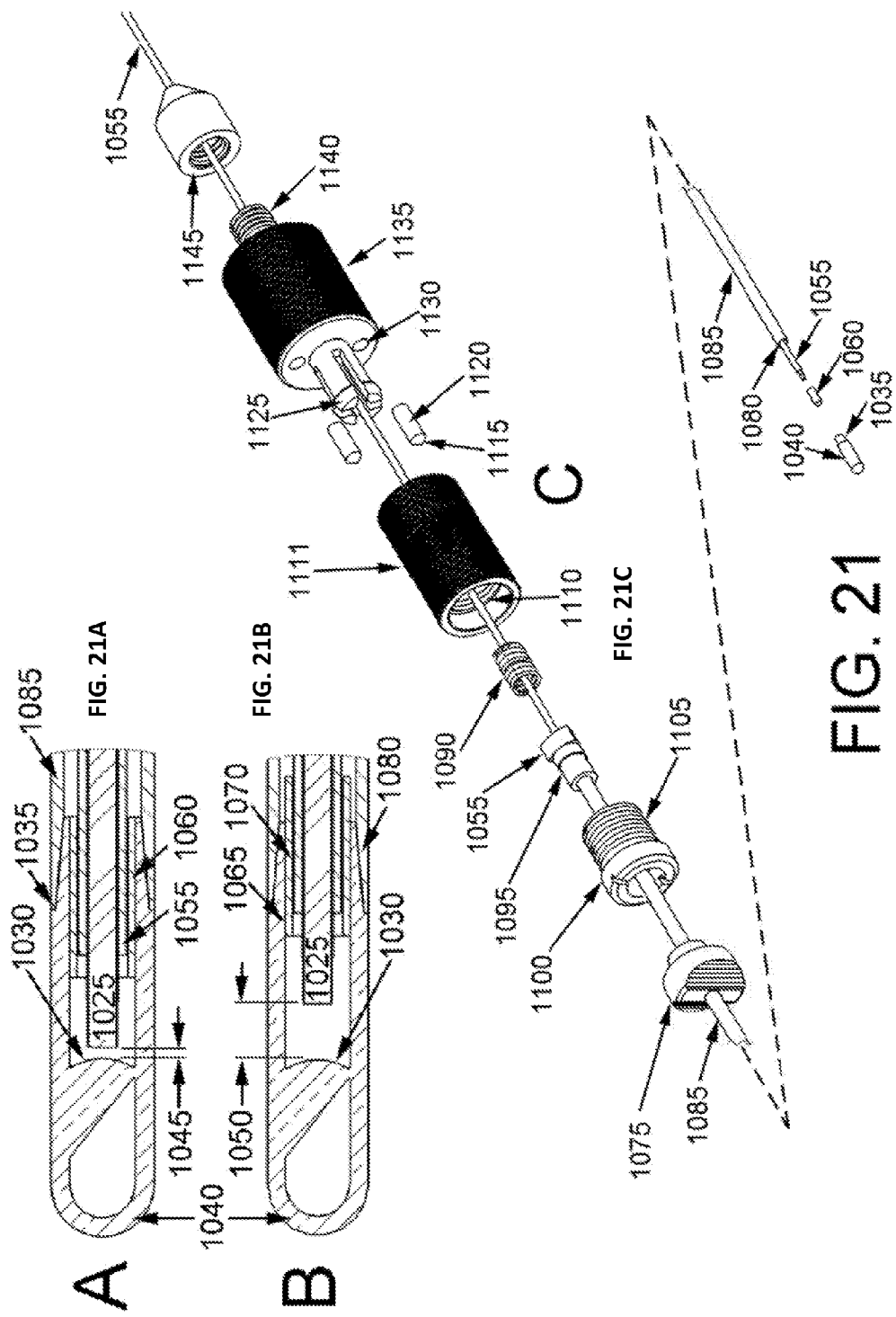
FIG. 21 illustrates a focus control only embodiment of the invention (the same embodiment shown in FIG. 18 except the free cap rotation feature is disabled) where FIGS. 21A and 21B provide cross-section detail of the fiber positions within the cap and FIG. 21C offers an exploded, isometric view of the assembly details.

In further clarification of the separate, yet compatible functions of free rotation and focus control, FIG. 21 depicts the focus control embodiment separately from the free rotation. The transmitting fiber 1055 is again secured within the pin vise jaws 1140 portion of the main body 1135 by tightening the pin vise cap 1145. In this instance, the free rotation shown in FIG. 20 can be defeated by loading the spring holes 1130 in the main body 1135 with cone-tipped 1115 pins 1120 that penetrate the fluted annular groove (see 985 in FIG. 20) of the (not rotationally defeated) rotation control element 1111. The main body 1135 of the control device retains the defeated rotation control element 1111 within the main body 1135 by way of an expanding barb 1125 that seats upon an interior shelf within the rotation control element as depicted in FIG. 20. In this instance, the threaded plug 1100 for focus control differs from the threaded plug (950 in FIG. 20) for rotation control but, in both, the threads 1105 mate to the threads 1110 of the rotation control element 1111 (with rotation function defeated by the cone-tipped pins 1120, as described above).

The focus control threaded plug 1100 is keyed (788 in FIG. 18) to match a keyed cannula carrier 1095 (780 in FIG. 18) and captures the focus default position return spring 1090 below the internal keyway (788 in FIG. 18). The cannula 1085 or semi-rigid tube is fixed within the keyed cannula carrier 1095 and the cannula carrier key 1055 passes into the threaded plug 1100 keyway (788 in FIG. 18) and compresses the default focus return spring 1090. The cannula 1085 can be fixed to the keyed cannula carrier 1095 by, for example, solvent welding, application of an adhesive, crimping, or other fixative methods. The focus control button 1075 fits over the keyed cannula carrier 1095, capturing the threaded plug 1100 (the combination considered a focus control element) and, when depressed, moves the cannula carrier, and cannula contained within, in the proximal direction relative to the main body 1135 in which the fiber 1055 is fixed by the pin-vise jaws 1140. In one instance, focus control button 1075 is affixed to the keyed cannula carrier 1095, for example affixed by hermetically sealing, gluing, solvent welding, compression fitting, screwing onto, or other means.

Preferably, the cap 1040 is hermetically attached or affixed to the cannula 1085 via a stepped cap chamfer 1035 nested within the cannula chamfer 1080. In one instance, a centering sleeve 1060 is fixed to the fiber buffer 1055 at 1070 (as it is in FIG. 20) and not to the cap 1040 at 1065 so that the centering sleeve 1060 moves relative to the cap 1040 when the focus control button 1075 is actuated. That is, the centering sleeve 1060 moves with the cap 1035 and/or cannula 1085 the same direction and distance 1050 as the fiber tip 1025. The actuation of the focus control button 1075 toward the main body 1135 reduces the distance between the cap input face 1030 and the fiber tip 1025 from an unactuated distance 1050 (providing a convergent output 820 (FIG. 19A)) to an actuated distance 1045 (providing a divergent output 860 (FIG. 19B)).

Yet another embodiment is illustrated in FIG. 22; this embodiment includes a fiber with a replaceable patient contact portion 1260. Wth the release of medical device reprocessing validation guidelines by the FDA (spring of 2015), although non-binding, the burden for proving that no organic material is carried from patient to patient through reprocessed and re-sterilized medical devices has increased substantially. Grooves, threaded elements, pits and other features that may harbor prions or other organic material that is not destroyed or inactivated by sterilization, or even bacterial cells or viral particles that might escape lethal exposure to the sterilizing medium by virtue of inaccessibility within such recesses, are too problematic to validate such that the resposable medical device of the future will provide for total replacement of patient contacting components, whether the contact is direct (device to tissue) or indirect (tissue to transport medium to device).

Reprocessing by replacement of patient contacting components must be validated to not risk damage or contamination to interior components that are exposed during reprocessing and provide reproducible restoration of initial function without adverse effect to the safety or efficacy of the device. The embodiment described below and depicted in FIG. 22 meets these criteria and may be combined with any or all of the herein described embodiments (including, free rotation for precise aiming, focus control for optimum irradiance, and the combination of focus control and free rotation) and could also be produced as a standalone option.

Replacing the patient contacting components is most easily accomplished where those components are replaced together, as a subassembly. That subassembly 1260 (or replaceable patient contact portion) (FIG. 22C) is separable from the reusable portion 1265 of the fiber device. In one example, FIG. 22A, the fiber buffer 1170 is not affixed to the centering sleeve 1165 as in prior embodiments (as a precaution against accidental reprocessing of a device that is not intended for reprocessing). The centering sleeve 1165 is, instead, affixed within the lateral redirecting cap 1150 and the fiber 1160 (carrying the fiber buffer 1170) can move within the centering sleeve 1165.

The lateral redirecting cap 1150 (and centering sleeve 1165, indirectly) is secured or affixed to an outer cannula 1175 which is secured or affixed to a threaded plug 1185, the bore 1190 within which it terminates. The outer cannula and treaded plug can be affixed to one another by, for example, solvent welding, application of an adhesive, crimping, or the like. In one instance, the cannula and threaded plug (e.g., the subassembly 1260) are made of a different material or color than a rotation control element 1240 and/or a main body 1280; in another instance, the threaded plug 1230 of the subassembly 1260 includes alternative or unique threads (e.g., the threaded plug can have a different thread pitch, a different thread count, and/or a reverse rotation) which distinguish a resposable product from one designed for single use, preventing accidental reprocessing of a single use device. When the subassembly 1260 is affixed to the rotation control element 1240 and/or main body 1280 an inner cannula 1180 is disposed within the bore of the outer cannula 1175 and about the fiber buffer 1170. The inner cannula 1180 is, preferably, affixed to the main body 1280 within bore 1295. As shown in FIG. 22A the inner cannula 1180 can extend past an end of the outer cannula 1190 (within the threaded plug 1185) and into the bore 1195 of the main body 1270 and, for example, terminating at 1205. Notably, the inner cannula can be affixed to a second threaded cap which is then affixed to a main body; further attachments and method of affixing the inner cannula to a main body can be accomplished.

In an example, the fiber can be equipped with a sleeve 1210 that is smaller than the main body bore 1195, in one example made of metal and crimped to the fiber buffer 1170, such that the sleeve 1210 abuts the inner cannula 1180 at a contact point 1205 when the fiber tip 1200 is in a working position. The working position being a position where the fiber tip 1235 is exposed and extends beyond an end of the inner cannula 1180. Notably and in reference to the embodiments provided above, the fiber tip 1200 is in a working position when it is positioned at the unactuated distance (e.g., 1050 FIG. 21) or the actuated distance (1045 FIG. 21). Preferably, the fiber tip 1200 is in a working position within the cap 1150 (a position that must be accurately reproduced after reprocessing). In another instance and as shown in prior embodiments, the fiber 1170 can be secured to the main body 1270 at the pin vise jaws 1220.

FIG. 22A depicts the fiber tip 1200 in a working position with the sleeve 1210 abutting the inner cannula 1180 at the contact point 1205. Preferably, the main body 1270 include a volume distal from the fiber tip 1200 and adjacent to the sleeve 1210 adapted to receive the sleeve 1210 and transition the fiber tip 1200 from a working position to a protected position.

FIG. 22B depicts the fiber tip 1200 in a protected position with a volume 1275 capable of receiving the sleeve 1210 between the inner cannula 1180 and the contact point 1205. In one example, the fiber tip 1200 during removal and replacement of the subassembly 1260 of the device can be retracted into the inner cannula 1300 before removing the resposable portion. This can be accomplished by loosening the pin vise jaws 1250, freeing the fiber 1275 to move within the main body 1280, and then sliding the metal sleeve 1285 until it stops at the bottom 1290 of the main body 1280 bore 1295. Wth the delicate fiber tip 1235 now protected within the inner cannula 1300, the pin vise jaws 1250 can be secured, the threaded plug 1230 can be unscrewed from the rotation control element 1240, and the outer cannula 1225, carrying the lateral redirecting cap 1305 (and threaded plug 1230) can be removed from the inner cannula 1300 without risk of damage or contamination to the bare fiber tip 1235.

Reassembly is performed in the reverse. The replacement subassembly 1260 is aligned with the reusable assembly 1265 as depicted in FIG. 22C, the inner cannula is threaded into the outer cannula and is advanced toward the cap until the threaded plug may be screwed into the rotation control element and secured. The fiber is then pushed distally at the pin vise until the metal sleeve stops on the inner cannula; the pin vise is tightened, producing a refreshed side fire fiber assembly; and the device is ready for sterilization and reuse.

Output orientation markings on side firing fibers have become de rigueur in recent years. While output orientation marks are potentially useful, their utility is typically limited to insuring that the side fire fiber cap is sufficiently extended from the endoscopic channel such that the endoscope is not damaged by scattered emissions, particularly where the markings are provided by printed heat shrink tubing about the cap, e.g. Vention Medical's Advanced Polymers printed PET, (generally extending proximally onto the transmitting fiber conduit for one to two inches). Heat shrink markers are rarely perfectly aligned about the circumference of the cap and very often are not well aligned to the fiber longitudinal axis.

One fiber with superior markings is the Lumenis Duo-Tome™ SideLite™. The protective transparent capsules of the DuoTome are substantially surrounded by a windowed stainless steel tubes (for protection) upon which various engraved marks are deployed for orientation of the output beam with respect to target tissues. Of course, where the tip (cap) of the fiber is completely opaque, as is the case with the DuoTome, orientation of the output must either really upon the clarity of the aiming beam spot on the tissue— clarity that is not particularly good in the DuoTome, or most fibers following a few tens of thousands of joules having been delivered—and the precision and accuracy of the accessory orientation marks. Engraved marks are very accurate.

The troubles with printed heat shrink markers are manifold but somewhat competing. Thinner wall heat shrink tubing, e.g. 0.00025 inches, tends toward distortion in application to the fiber and cracks if there are substantial gaps or diameter differences between the protective cap and the transmitting fiber, where thicker wall tubing, e.g. 0.003 inches, provides clear and well positioned marks and resists cracking, but adds considerable thickness to the cap outer diameter where clearance is already problematic. Further, the polyethylene terephthalate (PET) heat shrink is the first thermally labile material to be destroyed when side fire fiber caps overheat and devitrify, substantially disappearing just as the need for orientation cues becomes most important.

One roadblock for potentially resposable protective caps in prior art side fire fibers is a reliance on surgeons or medical technicians to reapply or realign output orientation markings on the fiber with the actual fiber output, or in the case of a stainless steel secondary cap like that of DuoTome, align the fiber output with the output window in the stainless steel. As used herein, "resposable" means a device in which a component, such as a surgical tip or blade, is optionally disposable and in which one or more other components, such as a holding member for the optionally disposable part, is reusable. This roadblock, the problems with alignment, marker tube cracking and addition to overall thickness are overcome with the new art single use and resposable fiber embodiments.

FIG. 23 depicts the subassembly (1260 in FIG. 22) of a resposable embodiment of the invention, where the lateral redirecting cap 1400 is decorated with a thin, yet refractory metallic orientation mark 1410, preferably made of gold, platinum or palladium, which is located on the lateral redirecting cap 1400 at a position that is 180° opposite an output direction 1415. The metallic mark 1410 is aligned 1405 with a second mark 1420 that is carried upon the cannula 1430, for example imprinted or engraved upon the cannula or co-extruded with the cannula. The depicted orientation marks afford improved orientation for the surgeon, beyond that offered in prior art, by extending proximally to the threaded plug 1440 and providing extracorporeal orientation information for the in vivo end of the device. A co-extruded or imprinted mark 1420 is preferably a universally recognized safe color such as green. A warning color such as red may be imprinted or co-extruded 180° opposite the safe color to ward against inadvertent inverse orientation.

Although the present invention has been described with reference to preferred embodiments, workers skilled in the art will recognize that changes may be made in form and detail without departing from the spirit and scope of the invention.

What is claimed:

1. A lateral redirecting device comprising:
   a lateral redirecting cap having a one-piece construction consisting of fused quartz and/or fused silica, including a guide section and an open-end section, the open-end section and the guide section divided by a lens, the open-end section including a bore which terminates at the lens, the open-end section shaped to receive a fiber optic cable, the guide section including a light path from the lens to a reflecting surface and then to a transmitting surface, the reflecting surface configured to direct electromagnetic radiation from the lens through the transmitting surface at a side of the lateral redirecting cap;
   the lateral redirected cap affixed to a cannula.

2. The lateral redirecting device of claim 1, wherein the cannula is further affixed to a threaded plug.

3. The lateral redirecting device of claim 1, wherein the cannula is an outer cannula, wherein the outer cannula is affixed to a threaded plug;
   the lateral redirecting device further comprising an inner cannula affixed to a main body, a transmitting optical fiber carried within the inner cannula, the inner cannula carried within the outer cannula, and the threaded plug affixed to the main body.

4. The lateral redirecting device of claim 1, wherein an output face of a transmitting optical fiber is proximal to an input face of the lens and within the open-end section of the lateral redirecting cap; the transmitting optical fiber carried within the cannula.

5. The lateral redirecting device of claim 1, wherein the cannula is affixed to a rotation control element, the rotation control element adapted to rotate the cannula, to which the lateral redirecting cap is affixed, relative to a main body.

6. The lateral redirecting device of claim 5, wherein an output face of a transmitting optical fiber is proximal to an input face of the lens and within the open-end section of the lateral redirecting cap; the transmitting optical fiber carried within the cannula; and wherein the rotation control element is adapted to rotate the cannula about the transmitting optical fiber.

7. The lateral redirecting device of claim 5, wherein the rotation control element is carried by a main body element to which the transmitting optical fiber is affixed.

8. The lateral redirecting device of claim 5, wherein the cannula is affixed to a focus control element, the focus control element adapted to translate the cannula and lateral redirecting cap in a longitudinal direction about a transmitting optical fiber; the focus control element carried by the rotation control element.

9. The lateral redirecting device of claim 8, wherein an output face of a transmitting optical fiber is proximal to an input face of the lens and within the open-end section of the lateral redirecting cap; the transmitting optical fiber carried within the cannula; wherein the rotation control element is adapted to rotate the cannula about the transmitting optical fiber; and wherein the focus control element adapted to translate the cannula and lateral redirecting cap in a longitudinal direction about the transmitting optical fiber.

10. The lateral redirecting device of claim 1, wherein the cannula is affixed to a focus control element, the focus control element adapted to translate the cannula and lateral redirecting cap in a longitudinal direction about a transmitting optical fiber.

11. The lateral redirecting device of claim 10, wherein the focus control element is affixed to a rotation control element.

12. The lateral redirecting device of claim 1, wherein a metallic orientation mark, disposed upon the lateral redirecting cap at a position 180° about the circumference from the transmitting surface, is aligned with a second orientation mark disposed upon the cannula and extending the entire length thereof.

13. The lateral redirecting device of claim 12, wherein the cannula is further affixed to a threaded plug.

14. A lateral redirecting device comprising:
   a transmitting optical fiber affixed to a main body; the main body carrying a cannula, wherein the transmitting optical fiber is positioned within the cannula; the cannula carrying a lateral redirecting cap having a lateral output; the transmitting optical fiber having an fiber output face proximal to a lens input carried by the lateral redirecting cap;
   the lateral redirecting device adapted to rotate the cannula and lateral redirecting cap relative to the main body without rotating the transmitting optical fiber and/or adapted to reduce a fiber-lens separation;
   wherein a direction of the lateral output rotates with the rotation of the cannula and lateral redirecting cap without rotation of the transmitting optical fiber.

15. The lateral redirecting device of claim 14, wherein the lateral redirecting device is adapted to rotate the cannula and lateral redirecting cap relative to the transmitting optical fiber; wherein the cannula is attached to a rotation control element which is affixed to the main body; the rotation control element adapted to produce a feedback to an operator upon rotation.

16. The lateral redirecting device of claim 14, wherein the lateral redirecting device is adapted to reduce a fiber-lens separation; wherein the cannula is attached to a focus control button; wherein actuation of the focus control button toward the main body reduces the fiber-lens separation distance.

17. A lateral redirecting device comprising:
   a transmitting optical fiber affixed to a main body; the main body carrying a cannula, wherein the transmitting optical fiber is positioned within the cannula; the cannula carrying a lateral redirecting cap having a lateral output; the transmitting optical fiber having an fiber output face proximal to a lens input carried by the lateral redirecting cap;
   the lateral redirecting device (A) adapted to increase a fiber-lens separation or (B) adapted to rotate the cannula and lateral redirecting cap relative to the main body without rotating the transmitting optical fiber and adapted to increase a fiber-lens separation.

18. The lateral redirecting device of claim 17, wherein the lateral redirecting device is adapted to rotate the cannula and lateral redirecting cap relative to the transmitting optical fiber; wherein the cannula is attached to a rotation control element which is affixed to the main body; the rotation control element adapted to produce a feedback to an operator upon rotation.

19. The lateral redirecting device of claim 17, wherein the lateral redirecting device is adapted to increase a fiber-lens separation; wherein the cannula is attached to a focus control button; wherein actuation of the focus control button away from the main body increases the fiber-lens separation distance.

* * * * *